United States Patent
Hage et al.

(10) Patent No.: US 8,268,570 B2
(45) Date of Patent: Sep. 18, 2012

(54) RESTRICTED ACCESS MEDIA AND METHODS FOR MAKING RESTRICTED ACCESS MEDIA

(75) Inventors: David S. Hage, Hickman, NE (US); Chunling Wa, Elmhurst, NY (US); Abby Jackson, Lincoln, NE (US); Hai Xuan, Rolla, MO (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 388 days.

(21) Appl. No.: 12/547,131

(22) Filed: Aug. 25, 2009

(65) Prior Publication Data
US 2010/0055667 A1 Mar. 4, 2010

Related U.S. Application Data

(60) Provisional application No. 61/092,546, filed on Aug. 28, 2008.

(51) Int. Cl.
*G01N 33/53* (2006.01)
(52) U.S. Cl. .......................... 435/7.1; 435/7.2; 436/518
(58) Field of Classification Search .................. None
See application file for complete search history.

(56) References Cited

U.S. PATENT DOCUMENTS

| | | | | |
|---|---|---|---|---|
| 4,208,479 | A * | 6/1980 | Zuk et al. | 435/7.9 |
| 5,082,929 | A * | 1/1992 | Ngo et al. | 530/391.1 |
| 6,500,671 | B2 | 12/2002 | Hage et al. | |
| 6,727,104 | B2 | 4/2004 | Hage et al. | |
| 7,833,723 | B2 * | 11/2010 | Bian et al. | 435/7.1 |
| 2002/0151086 | A1 | 10/2002 | Hage et al. | |

OTHER PUBLICATIONS

Morag et al. (Analytical Biochem 1996 vol. 243, p. 257-263).*
Clark et al., "Analysis of Free Drug Fractions by Ultrafast Immunoaffinity Chromatography", Anal. Chem., 2001, pp. 2157-2164, vol. 73.
Clark et al., "Development of Sandwich HPLC Micro Columns for Analyte Adsorption on the Millisecond Time Scale", Anal. Chem., 2001, pp. 1366-1373, vol. 73.
Larsson et al., "High-Performance Liquid Affinity Chromatography", Methods Enzymol, 1984, pp. 212-223.
Ruhn et al., "Development of Dihydrazide-Activated Silica Supports for High-Performance Affinity Chromatography", J. Chromatog. 1994, pp. 9-19, vol. 669.
Rudolphi et al., "The Use of Restricted-Access Media in HPLC, Part II, Applications", LC-GC, 1997, pp. 814, 817-818, 820, 822-823, vol. 15 No. 9.
Clark et al., "Analysis of Free Hormone Fractions by an Ultrafast Immunoextraction/Displacement Immunoassay: Studies Using Free Thyroxine as a Model System", Anal. Chem. 2005, pp. 1859-1866, vol. 77.
Jiang et al., "Affinity Monoliths for Ultrafast Immunoextraction" Anal. Chem., 2005, pp. 2362-2372, vol. 77.
Ohnmacht et al., "Analysis of Free Drug Fractions Using Near-Infrared Fluorescent Labels and an Ultrafast Immunoextraction/Displacement Assay", Anal. Chem., 2006, pp. 7547-7556, vol. 78.

* cited by examiner

*Primary Examiner* — Jacob Cheu
(74) *Attorney, Agent, or Firm* — Thompson Coburn LLP

(57) ABSTRACT

The present invention is directed to restricted access media (RAM), methods for preparing restricted access media, and kits for preparing restricted access media that contain protected ligand binding agents or protected enzymes. Certain RAM provided contain a plurality of protected regions of the support that contain ligand binding agents that are protected by blocking agents. Certain RAM provided contain a plurality of protected regions of the support that contain unbound ligand binding agents or enzymes that are retained in the protected regions by a capping agent. Methods of making the RAM of the invention and associated kits are also provided.

11 Claims, 12 Drawing Sheets

Preparation of restricted access medium using antibody as the ligand binding agent molecule.

Effect of support pore size on the percentage of $F_{ab}$ regions retained.

Effect of support pore size on the percentage of $F_{ab}$ regions remaining following cleaving agent treatment.

Effect of cleaving agent concentration.

Retention of fluorescein or fluorescein-BSA by an anti-fluorescein restricted access media.

(a) Fluorescein (b) Fluorescein-BSA Conjugate

Percent extraction of fluorescein or fluorescein by an anti-fluorescein restricted access media.

Restricted access media with protected and unbound protein.

(a) Reaction between oxidized glycogen and a hydrazide-activated support (b) Retention of a protein as oxidized glycogen reacts with a hydrazide-activated support Amount of Human Serum Albumin retained using a hydrazide-activated support with pore sizes ranging from 50 Å to 1000 Å.

RESTRICTED ACCESS MEDIA AND METHODS FOR MAKING RESTRICTED ACCESS MEDIA

CROSS-REFERENCE TO RELATED APPLICATIONS

This application claims the benefit of U.S. Provisional Patent Application No. 61/092,546 filed Aug. 28, 2008 under 35 USC 119(e) and incorporated herein by reference in its entirety.

STATEMENT REGARDING FEDERALLY SPONSORED RESEARCH OR DEVELOPMENT GOVERNMENTAL SUPPORT

This invention was made with Government support under Grant #R01 GM044931 and Grant #R01 DK069629, both awarded by the National Institutes of Health. The government has certain rights to this invention.

BACKGROUND OF THE INVENTION

Restricted access media (RAM) have been used for many years in work with biological samples to combine the features of size exclusion chromatography with partition or ion-exchange chromatography. The support in RAM is typically porous silica or a porous polymer having a non-adsorptive and hydrophilic outer surface and an interior stationary phase that can retain analytes through partitioning or ionic interactions. This provides a medium in which only low mass substances are retained, while larger agents such as proteins elute in the excluded volume. RAM have been used for analysis of drugs, peptides, and endogenous substances in complex samples such as serum, blood, urine, and cell cultures.

Many small molecules such as drugs and hormones bind proteins and/or other agents that are present in a sample. This gives rise to both a free (non-bound) form and a bound form of the small molecule in the sample. Traditional methods for separating free and bound forms of small molecules include equilibrium dialysis and ultrafiltration, which can involve long analysis times, are often labor intensive, and usually require additional analytical methods for actual measurement of the free form. These methods involve a size separation between the free form and bound form. Non-affinity restricted access media columns have been used for separation of free and bound forms, however, these columns have given only partial separation and work for only some analytes. Ultrafast extraction of free forms by small immobilized antibody columns have been reported, however, these assays require using an antibody support that can recognize and bind the free form without having significant interactions with the bound form. Accordingly, a need exists for a media having high selectivity towards free forms of the small molecule but without significant interactions with bound forms and methods for making these media.

One challenge presented by immobilized or covalently linked molecules is to attach them to supports while retaining their behavior in their native form. Covalently linking or immobilization of molecules directly to the support may affect the molecule's activity if the molecule is linked at or near its active site. For example, antibodies attached to a support by their $F_{ab}$ fragment may decrease and/or lose their ability to bind antigen. Covalent immobilization may also result in multisite attachment and random orientation of the molecule, which often leads to decreased or complete loss of activity. Noncovalent immobilization techniques can involve the adsorption of a ligand binding agent to a surface, the binding of one ligand binding agent to a second ligand binding agent, or the formation of a complex between the ligand binding agent and support. Entrapment or encapsulation techniques involve the physical containment of a molecule in a support. Previously described entrapment methods are limited to particular types of supports (i.e., sol gels) and are useful only with relatively small volume systems (i.e., capillary columns in HPLC). Accordingly, a need exists for non-covalent retention of molecules that is applicable to a variety of different support materials and molecules to produce supports containing noncovalently linked agents that closely mimic the behavior of these same agents in their native unbound form.

SUMMARY OF THE INVENTION

The invention generally relates to Restricted Access Media that comprise protected ligand binding agents or enzymes and methods of making such Restricted Access Media supports. In certain embodiments, the present invention provides new RAM supports and methods for making RAM supports. In one aspect, the RAM supports contain covalently bound ligand binding agent molecules in protected regions. Another aspect provides methods for preparing a restricted access media containing covalently bound ligand binding agent molecules in protected regions. In another aspect, the RAM supports contain unbound ligand binding agent or enzyme molecules retained by a capping agent. A further aspect provides methods for preparing a restricted access media containing unbound ligand binding agent or enzyme molecules retained by a capping agent.

In certain embodiments, the invention provides a restricted access media comprising a support wherein a plurality of protected regions of said support contain one or more covalently linked ligand binding agent molecule(s) and wherein a plurality of unprotected regions of said support contain one or more covalently linked blocking agent molecule(s). In certain embodiments, the support can comprise an inorganic material, a biological material, an organic material, an organic polymer, a composite support, or a modified support. In certain embodiments, the support can comprise silica, glass, alumina, zirconia, silver, gold, agarose, dextran, cellulose, polystyrene, polymethacrylate, polyamide, agarose-coated quartz, agarose-coated stainless steel, or coated polystyrene/divinylbenzene. In certain embodiments, the ligand binding agent molecule can comprise a protein, a glycoprotein, a DNA, a RNA, a nucleoprotein, or a carbohydrate containing agent. In certain embodiments, the blocking agent molecule can comprise a sub-fragment of the ligand binding agent molecule wherein ligand binding activity is reduced or eliminated. In certain embodiments, the blocking agent molecule can also comprise a sub-fragment of a linking agent. In certain embodiments, the linking agent can comprise a carbohydrate, a nucleic acid, or a peptide.

In certain embodiments, the invention provides methods for preparing a restricted access media comprising incubating an activated support with a solution comprising a plurality of ligand binding agent molecules to form a ligand bound support wherein the ligand binding agent molecule is covalently linked to the support; treating the ligand bound support with a size restricted cleaving agent that cleaves one or more ligand binding agent molecule(s) or one or more linking agent molecules bound to unprotected regions of the support; and removing the cleaving agent and unbound fragments of cleaved ligand binding agent molecules or linking agent molecules, thereby preparing a restricted access media. In certain embodiments, the support can comprise silica, glass, alumina, zirconia, silver, gold, agarose, dextran, cellulose, polystyrene, polymethacrylate, polyamide, agarose-coated quartz, agarose-coated stainless steel, or coated polystyrene/divinylbenzene. In certain embodiments, the support can comprise a pore size in the range of about 50 Å to about 500 Å. In certain embodiments, the size restricted cleaving agent can comprise an enzyme or ribozyme. In certain embodiments, the ligand binding agent molecule can comprise a protein, a glycoprotein, a DNA, a RNA, a nucleoprotein, or a carbohydrate containing agent. In certain embodiments, the ligand binding agent molecule can be covalently linked to the support by an amine group, a sulfhydryl group, a carboxylate group, a carbonyl group, or a combination thereof. In certain embodiments, the ligand binding agent molecule can further comprise an activated ligand binding agent molecule. In certain embodiments, the linking agent can comprise a protein, a glycoprotein, a DNA, a RNA, a nucleoprotein, or a carbohydrate containing agent. In certain embodiments, the size restricted cleaving agent can comprise a protease. In certain embodiments, the protease can comprise a cysteine protease, a serine protease, a threonine protease, an aspartate protease, or a metalloprotease. In certain embodiments, the activated support can be activated by an aldehyde or a hydrazide.

In certain embodiments, the invention provides restricted access media comprising a support wherein a plurality of protected regions of the support contain one or more unbound ligand binding agent(s) or enzyme molecules and wherein the ligand binding agent(s) or enzyme molecule(s) are retained in the protected regions by a capping agent. In certain embodiments, the protected region of the support can be on a surface, in an interior pore, or a combination thereof. In certain embodiments, the support can comprise an inorganic material, a biological material, an organic material, an organic polymer, a composite support, or a modified support. In certain embodiments, the support can comprise silica, glass, alumina, zirconia, silver, gold, agarose, dextran, cellulose, polystyrene, polymethacrylate, polyamide, agarose-coated quartz, agarose-coated stainless steel, or coated polystyrene/divinylbenzene. In certain embodiments, the unbound ligand binding agent can comprise a protein, a glycoprotein, a DNA, a RNA, a nucleoprotein, a carbohydrate containing agent, a lipoprotein, or a combination thereof. In certain embodiments, the capping agent can comprise a glycoprotein, a glycolipid, a carbohydrate containing agent, or a combination thereof. In certain embodiments, the carbohydrate containing agent can comprise glycogen, dextran, agarose, or cellulose.

In certain embodiments, the invention provides methods for preparing a restricted access media comprising incubating an activated support with a solution comprising: i) a ligand binding agent or an enzyme molecule and ii) an activated capping agent; and removing unbound capping agent from said incubated support, thereby preparing the restricted access media comprising a support wherein a plurality of protected regions of said support contain one or more unbound ligand binding agent(s) or enzyme molecule(s) and wherein said ligand binding agent(s) or enzyme molecule(s) are retained in said protected regions by said capping agent. In certain embodiments, the method can further comprise washing the restricted access media with a solution to deactivate bound capping agent. In certain embodiments, the solution to deactivate bound capping agent can comprise a hydrazide-containing agent or an amine-containing agent. In certain embodiments, the protected region of the activated support is on a surface, in an interior pore, or a combination thereof. In certain embodiments, the ligand binding agent or the enzyme molecule and the activated capping agent can be incubated together with the activated support or incubated separately with the activated support. In certain embodiments, the activated support can comprise silica, glass, alumina, zirconia, silver, gold, agarose, dextran, cellulose, polystyrene, polymethacrylate, polyamide, agarose-coated quartz, agarose-coated stainless steel, or coated polystyrene/divinylbenzene. In certain embodiments, the activated support can be activated by a hydrazide group, an amine group, an aldehyde group, or a combination thereof. In certain embodiments, the activated capping agent can comprise a glycoprotein, a glycolipid, or a carbohydrate-containing agent. In certain embodiments, the carbohydrate containing agent can comprises glycogen, dextran, agarose, or cellulose. In certain embodiments, the activated capping agent can be activated by oxidization with an oxidizing agent. In certain embodiments, the oxidizing agent comprises a periodate, a periodate-related chemical, or an enzyme treatment. In certain embodiments, the activated capping agent can comprise an oxidized capping agent, a hydrazide-containing agent, an amine-containing agent, or hydrazine. In certain embodiments, the support can comprise a porous support with a pore size of about 50 Å to about 1000 Å. In certain embodiments, the enzyme molecule can comprise an oxidoreductase, a transferase, a hydrolase, a lyase, an isomerase, or a ligase.

In certain embodiments, the invention provides kits for preparing a restricted access media comprising: i) a support that is substantially free of ligand binding agent molecules and ii) a size restricted cleaving agent. In certain embodiments, the kits can further comprise any one of: 1) instructions for the use thereof, 2) a solution for activating the support, 3) an activated support, 4) a ligand binding agent molecule that is not covalently linked to the support or a linking agent that is not covalently linked to the support; or any combination of elements 1, 2, 3, and/or 4. In certain embodiments of any of the foregoing kit embodiments, the restricted access media that is prepared comprises a support wherein a plurality of protected regions of said support contain one or more covalently linked ligand binding agent molecules and wherein a plurality of unprotected regions of said support contain one or more covalently linked blocking agent molecule(s).

In certain embodiments, the invention provides kits comprising restricted access media comprising: i) a support wherein a plurality of protected regions of the support contain one or more covalently linked ligand binding agent molecules and wherein a plurality of unprotected regions of the support contain one or more covalently linked blocking agent molecule(s) and ii) at least one container. In certain embodiments, the kits can further comprise instructions for the use thereof.

In certain embodiments, the invention provides kits for preparing a restricted access media comprising: i) a support that is substantially free of ligand binding agent or enzyme molecules, and ii) a capping agent. In certain embodiments, the kits can further comprise any one of: 1) a solution for activating the capping agent; 2) a solution for activating said support; 3) instructions for the use thereof; 4) an activated support; 5) a ligand binding agent or an enzyme molecule that is not associated with the support; or any combination of elements 1, 2, 3, 4, and/or 5. In certain embodiments of any of the foregoing kit embodiments, the restricted access media that is prepared can comprise a support wherein a plurality of protected regions of the support contain one or more unbound ligand binding agent(s) or enzyme molecule(s) and wherein the ligand binding agent(s) or enzyme molecule(s) are retained in the protected regions by a capping agent.

In certain embodiments, the invention provides kits comprising a restricted access media comprising: i) a support wherein a plurality of protected regions of the support contain one or more unbound ligand binding agent or enzyme molecules and wherein the ligand binding agent(s) or enzyme molecules are retained in the protected regions by a capping agent, and ii) at least one container. In certain embodiments, the kits can further comprise instructions for the use thereof.

BRIEF DESCRIPTION OF THE DRAWINGS

FIG. 4($b$) is bar graph showing the percentage of $F_{ab}$ regions remaining versus nominal pore size of the support.

DETAILED DESCRIPTION

Definitions

Figure 1:
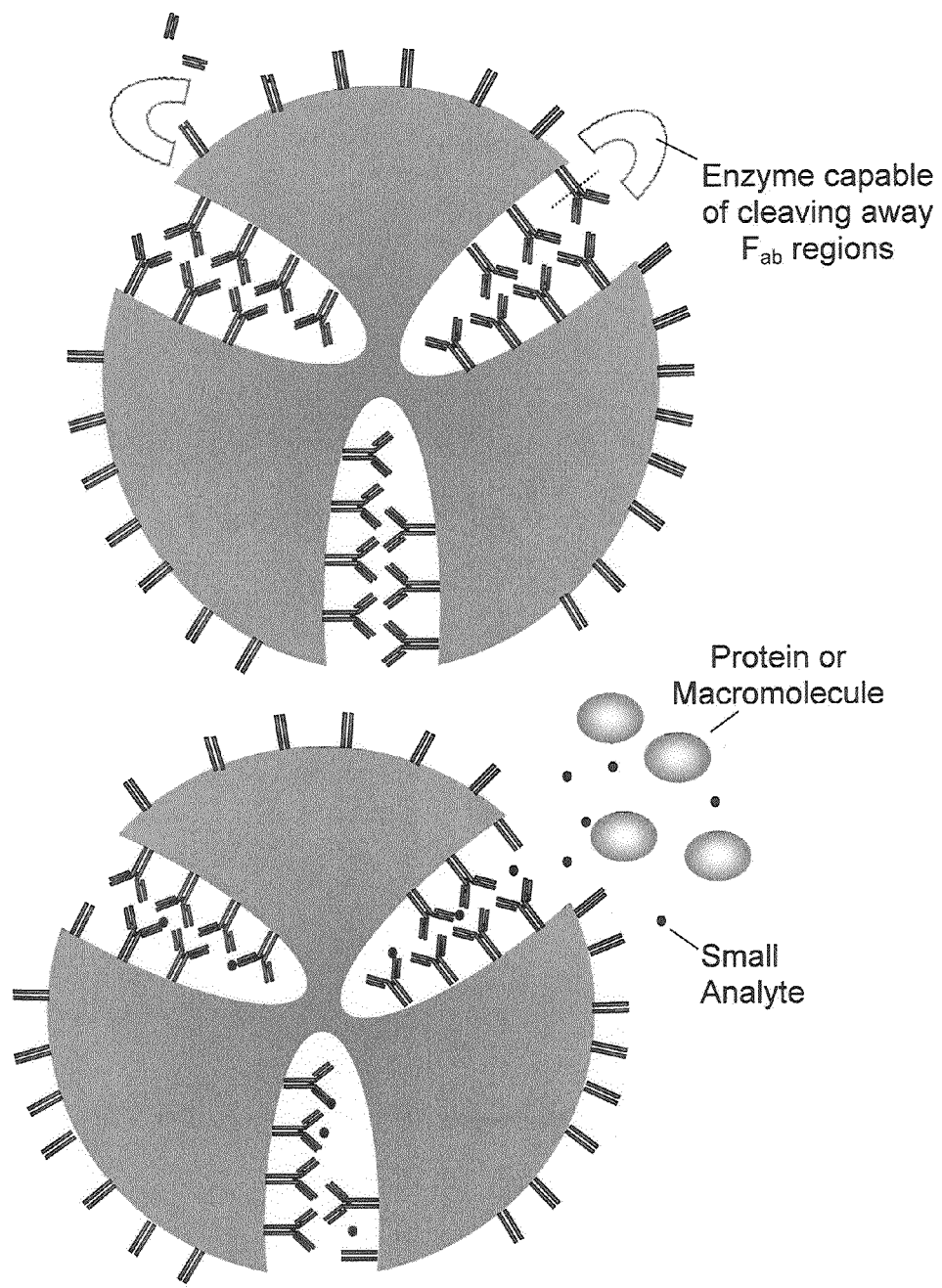
FIG. 1 is an illustration showing the preparation of a Restricted Access Medium.

As used herein, the phrase "ligand binding agent molecule(s)" refers to one or more molecules that can sequester another molecule or "target" from a solution. Ligand binding agent molecules include, but are not limited to, a protein, a glycoprotein, a DNA, a RNA, a nucleoprotein, or a carbohydrate-containing agent.

The terms "protein," "peptide," and "polypeptide" are used interchangeably herein to refer to a polymer of amino acid residues of any length.

As used herein, the phrase "blocking agent molecule(s)" refers to a molecule that is covalently linked to a support to create a protected region in or upon the support. A blocking agent molecule can include, but is not limited to, a cleaved sub-fragment of a ligand binding agent molecule resulting from treatment with a cleaving agent, leaving only a sub-fragment of the ligand binding agent molecule covalently linked to a support. In certain embodiments, the sub-fragment of the ligand binding agent molecule that is linked to the support following cleavage is a sub-fragment where ligand binding activity is reduced. In certain embodiments, the sub-fragment of the ligand binding agent molecule that is linked to the support following cleavage is a sub-fragment where ligand binding activity is eliminated. In still other embodiments, the sub-fragment of the ligand binding agent molecule that is linked to the support following cleavage is a sub-fragment where a ligand binding domain has been removed or has been disrupted. In certain embodiments, the sub-fragment of the ligand binding agent molecule that is linked to the support following cleavage can be further modified using a chemical reagent or second binding agent to reduce non-specific binding. In other embodiments, a blocking agent molecule can be a different molecule than the ligand binding agent molecule. In certain embodiments where the blocking agent molecule is different than the ligand binding agent molecule, the blocking agent molecule can be a sub-fragment of a linking agent. As used herein, a "linking agent" refers to a molecule that is conjugated to the ligand binding agent molecule and is used to attach the ligand binding agent molecule to the support. Linking agents include, but are not limited to, carbohydrates, nucleic acids, and peptides.

As used herein, the phrase "capping agent" refers to a molecule that is used to retain an unbound ligand binding agent or enzyme in a protected region.

As used herein, the phrase "protected region" refers to an area or space of a support that contains either one or more ligand binding agent molecule(s) or enzyme molecules such that access to the contained molecules is restricted to molecules within a desired molecular weight range. A "protected region" includes, but is not limited to, a pore, a space, a gap, an opening, a hole, a crack, a fissure, a cavity, a pit, a crater, a cleft, a crevice, or combinations thereof.

As used herein, the phrase "unprotected region" refers to an area or space of a support that is large enough to be accessible by a cleaving agent. In the context of a RAM media comprising one or more covalently linked ligand binding agent molecule(s) in a protected region, a region occupied by one or more blocking agent molecule(s) following enzyme or protease treatment would represent an "unprotected region." In the case where the ligand binding agent molecule is an antibody that is covalently linked to the support by its $F_c$ region, for example, the cleaved $F_c$ portion of the antibody molecule that remains following cleaving agent treatment resides in an "unprotected region".

As used herein, the phrases "covalently linked" and "covalent linkage" mean attached by a covalent bond. For example, an antibody can be covalently linked to an aldehyde-activated support by amine linkages between the antibody and the aldehyde-activated support.

As used herein, the term "conjugated" means joined together. Conjugation includes covalent linkages. For example, a linking agent can be conjugated to, or joined together with, a ligand binding agent molecule.

As used herein, the phrase "substantially free" refers to a composition wherein the undesired material is present at a final percent (i.e. weight undesired material/total composition weight) of at least less than about 1%.

Restricted Access Media Comprising Protected Covalently Linked Ligand Binding Agents Certain embodiments of the invention include restricted access media comprising a support wherein a plurality of protected regions of the support contain one or more covalently linked ligand binding agent molecule(s) and wherein a plurality of unprotected regions of the support contain one or more covalently linked blocking agent molecule(s). The support can be any support that can be used directly or in a modified form for ligand binding agent attachment and combinations thereof. In certain embodiments, supports can comprise an inorganic support material. Inorganic support materials can include, but are not limited to, silica, glass, alumina, zirconia, silver, and gold. In certain embodiments, supports can comprise a biological support material. Biological support materials can include, but are not limited to, agarose, dextran, and cellulose. Supports can comprise one or more organic support material(s) and organic polymer supports. Organic support materials and organic polymer supports can include, but are not limited to, polystyrene, polymethacrylate, and polyamide. In other embodiments, the support can comprise a composite support. Composite supports include, but are not limited to, an agarose coating on quartz, an agarose coating on stainless steel, and coated polystyrene/divinylbenzene. In other embodiments, the support can comprise a modified support. Modified supports can include, but are not limited to, silica, glass beads, polystyrene, gold, or silver that contain an added chemical group. Chemical groups used in modified supports include, but are not limited to, surface diol groups, aldehyde groups, hydrazide groups, amine groups, and sulfhydryl groups. Formats for the support can comprise porous or non-porous particles, planar surfaces, or flow-through supports. Other formats for the support can include, but are not limited to, monolithic materials or perfusion supports, membrane supports, capillaries, fibers, and expanded bed supports.

The ligand binding agent molecule can be a protein, a glycoprotein, a DNA, a RNA, a nucleoprotein, or a carbohydrate-containing agent. Without seeking to be limited by theory, a size-restricted cleaving agent, such as an enzyme, protease, or other agent, is unable to access the ligand binding agent molecule residing in protected regions. While again not seeking to be limited by theory, access of the size restricted cleaving agent can be restricted by electrostatic and/or steric hindrance. Thus, the size restricted cleaving agent cannot cleave the ligand binding agent molecule, leaving it uncleaved or intact. For example, the ligand binding agent molecule can be an antibody. As shown in FIG. 1(a) using an IgG antibody as the ligand binding agent molecule, the antibody is covalently linked to the support by the $F_c$ regions. Upon treatment with an enzyme capable of cleaving away $F_{ab}$ regions, the enzyme is inaccessible to the antibody molecule(s) residing in protected regions or excluded from the protected regions. Thus, the enzyme or protease cannot cleave antibody molecules residing in the protected regions, leaving those molecules uncleaved or intact.

A blocking agent molecule can be a sub-fragment of the ligand binding agent molecule. The blocking agent molecule can also be a sub-fragment of a linking agent. In certain embodiments, a linking agent is conjugated to the ligand binding agent molecule and is used to attach the ligand binding agent molecule to the support. Linking agents include, but are not limited to, carbohydrates, nucleic acids, and peptides.

In an exemplary embodiment, a nucleic acid linking agent can be conjugated to a ligand binding agent that can be a protein, a carbohydrate, or another nucleic acid. The nucleic acid linking agent—ligand binding agent conjugate can then be covalently linked to the support by the nucleic acid linking agent. The nucleic acid is then cleaved with a size restricted cleaving agent. The size restricted cleaving agent can be, for example, an enzyme such as a nuclease. When the ligand binding agent is also a nucleic acid, the nuclease can in certain embodiments be a site specific nuclease that selectively cleaves the nucleic acid linking agent. In this embodiment, the remaining sub-fragment of the nucleic acid that is linked to the support following nuclease cleavage is the blocking agent.

In another exemplary embodiment, a carbohydrate linking agent can be conjugated to a ligand binding agent that can be a protein or a nucleic acid. The carbohydrate—protein conjugate can then be covalently linked to the support by the carbohydrate linking agent. The carbohydrate is then cleaved by a size restricted cleaving agent. The size restricted cleaving agent can be, for example, an enzyme that cleaves the carbohydrate. In this embodiment, the remaining sub-fragment of the carbohydrate linking agent that is linked to the support following cleavage is the blocking agent.

In yet another exemplary embodiment, a peptide linking agent can be conjugated to the ligand binding agent that can be a nucleic acid, a carbohydrate, or another protein. The peptide linking agent—ligand binding agent conjugate can then be covalently linked to the support by the peptide linking agent. The peptide is then cleaved with a size restricted cleaving agent. The size restricted cleaving agent can be, for example, a protease or peptidase. When the ligand binding agent is also a protein, the protease or peptidase can in certain embodiments be a site specific protease or peptidase that selectively cleaves the peptide linking agent. In this embodiment, the remaining sub-fragment of the peptide that is linked to the support following cleavage is the blocking agent.

As described, the ligand binding agent can be attached either directly to the support or can be attached to the support with a linking agent. Without seeking to be limited by theory, the size restricted cleaving agent is able to access the ligand binding agent molecule or linking agent residing in or on unprotected regions and that is linked either directly or through a linking agent to the unprotected regions of the support. Thus, the size restricted cleaving agent cleaves the ligand binding agent molecule or linking agent. The sub-fragment of the cleaved ligand binding agent or linking agent that is covalently linked to the support forms the blocking agent molecule(s), whereby the fragment of the cleaved ligand binding agent or linking agent—ligand binding agent conjugate that is not covalently linked or is otherwise unbound to the support is removed. As shown in the non-limiting and exemplary embodiment depicted in FIG. 1(a), when using an IgG antibody as the ligand binding agent molecule, the antibody can be covalently linked to the support by the $F_c$ regions. Upon treatment with an enzyme capable of cleaving away $F_{ab}$ regions, the $F_{ab}$ sub-fragments of the antibody are cleaved from the antibody molecules residing in or on unprotected regions of the support. The $F_c$ region of the antibody molecule that is covalently linked to the support remains following enzyme treatment and forms the blocking agent molecule.

Methods for Preparing a Restricted Access Media Comprising Protected Covalently Linked Ligand Binding Agents Other embodiments of the invention include methods for preparing a restricted access media. Methods provided herein comprise incubating an activated support with a solution having a plurality of ligand binding agent molecules to form a ligand bound support wherein the ligand binding agent molecule is covalently linked to the support. The ligand bound support is treated with a size restricted cleaving agent that cleaves one or more ligand binding agent molecule(s) bound to unprotected regions of the support. The cleaving agent and unbound fragments of cleaved ligand binding agent molecules are removed, thereby preparing the restricted access media.

The ligand binding agent molecule can be a protein, a glycoprotein, a DNA, a RNA, a nucleoprotein, or a carbohydrate-containing agent. The ligand binding agent molecule can be, for example, an antibody. Alternatively, the ligand binding agent can be an aptamer or a lectin.

The ligand binding agent molecule(s) can be covalently linked to the support by an amine group, a sulfhydryl group, a carboxylate group, a carbonyl group, or a combination thereof. The ligand binding agent molecule(s) can also be activated prior to incubation with the support. For example, a ligand binding agent molecule having carbohydrate residues can be activated by oxidization of the carbohydrate residues. Activation by oxidization can be performed by treatment of the ligand binding agent molecule(s) with periodic acid, a periodate-related chemical, or an enzyme treatment. In other embodiments, the plurality of ligand binding agent molecules can comprise ligand binding agent molecules that are conjugated linking agents. In this embodiment, ligand binding agent molecules can be covalently linked to the support by a linking agent. Linking agents can be carbohydrates, nucleic acids, and peptides that can be attached to the support.

The activated support used in the method can be any support that can be used directly or in a modified form for ligand binding agent attachment and combinations thereof. The support can be, for example, inorganic support materials. Inorganic support materials can be, for example, silica, glass, alumina, zirconia, silver, and gold. The support also can be biological support materials. Biological support materials can be, for example, agarose, dextran, and cellulose. The support further can be organic support materials and organic polymer supports. Organic support materials and organic polymer supports can be, for example, polystyrene, polymethacrylate, and polyamide. The support can be composite supports. Composite supports can be, for example, agarose coating on quartz, agarose coating on stainless steel, and coated polystyrene/divinylbenzene. Modified supports can be, for example, silica, glass beads, polystyrene, gold, or silver that contain, for example, surface diol groups, aldehyde groups, hydrazide groups, amine groups, and sulfhydryl groups. Formats for the support can comprise porous or non-porous particles, planar surfaces, or flow-through supports. Other formats for the support can include, but are not limited to, monolithic materials or perfusion supports, membrane supports, capillaries, fibers, and expanded bed supports. An activated support can be an aldehyde-activated support or a hydrazide-activated support.

An aldehyde-activated support can be prepared according to a method adapted from Larsson (104 Methods Enzymol. 212-223 (1984)) and Ruhn et al., (669 J. Chromatogr. 9-19 (1994)). Briefly, for example, an aldehyde-activated support can be prepared by treating a porous silica support with a solution comprising an organic silane such as, 3-glycidoxypropyltrimethoxysilane, to introduce epoxy groups onto the support. The resulting epoxy groups are hydrolyzed by treating the support with a sodium acetate solution. After washing with water, the support is treated with an aqueous solution of sulfuric acid to convert epoxy groups to diol groups. The resulting diol support is treated with a solution of 90% (v/v) acetic acid and water containing 500 mg periodic acid and mixed for about two hours at room temperature to convert diol groups to aldehyde groups. The resulting aldehyde-activated support is washed with water followed by washing with a potassium phosphate buffer and stored until use.

To prepare a hydrazide-activated support, an aldehyde-activated support is treated with a potassium phosphate buffer containing about a 5-fold mole excess of oxalic dihydrazide (calculated using the initial diol groups present in the added support) with shaking for about 2 hours at room temperature. After several potassium phosphate buffer washes, about a 25-fold mole excess (calculated using the initial diol groups) of sodium borohydride in 0.1 M potassium phosphate buffered saline (PBS) is added in small portions to the slurry and incubated with shaking for about 90 minutes at room temperature to reduce any remaining aldehyde groups. The support is subsequently washed in potassium phosphate buffer and stored until use.

To form the ligand bound support wherein the ligand binding agent molecule is covalently linked to the support, an activated support is treated with a solution comprising a ligand binding agent molecule(s) to form a slurry. The amount of ligand binding agent molecule(s) used can be greater than the maximum amount that can be immobilized on the surface of the support and based on the surface area of the support and size of the ligand binding agent molecule(s). For example, if the ligand binding agent molecule is an IgG antibody, the amount used is about two-fold greater than the maximum amount that can be immobilized to the surface of the support, as determined by Clark et al., (888 J. Chromatog. 13-22 (2000)) and by calculations based on the known surface area of the support and size of IgG (see e.g., Walters et al. (140 Anal. Biochem. 190-195 (2000)). When an aldehyde-activated support is used, a solution such as an 8 mg/mL sodium cyanoborohydride solution, can be added to the slurry to promote formation of stable secondary amine linkages between the ligand binding agent molecule(s) and the support. When a hydrazide-activated support is used, the ligand binding agent molecule can be activated prior to addition to the support. When the ligand binding agent molecule is an IgG antibody for example, the antibody can be activated by oxidization with periodate to generate aldehyde groups in the carbohydrate regions. Preferably, cross-linked or precipitated immunoglobulins are removed from the final oxidized antibody solution prior to incubation with the activated support.

The activated support and ligand binding agent molecule slurry is incubated while shaking for 3 days at 4° C. The resulting support is washed with about 0.1 M potassium phosphate buffer (pH 8.0) and treated with a 4 mg/mL solution of sodium borohydride for about 90 minutes at room temperature to convert any remaining aldehyde groups into alcohols.

Figure 2A:
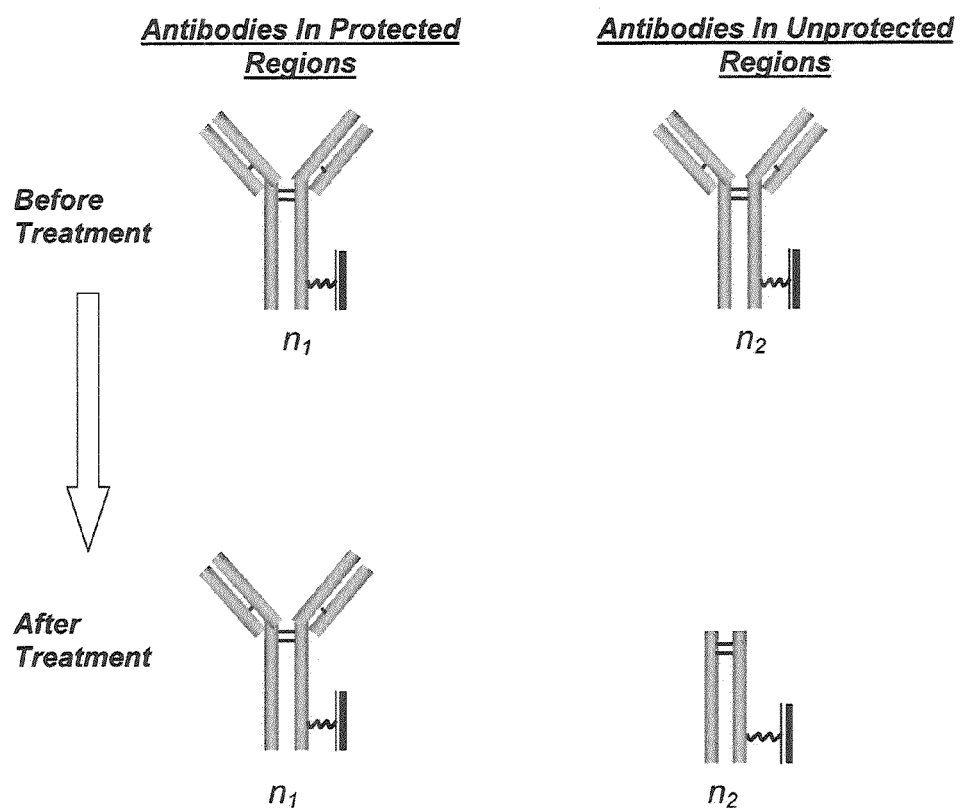
FIG. 2 is an illustration showing the structure of antibodies located in protected and unprotected regions of the support before and after enzyme treatment for (a) the hydrazide-activated support method and (b) the aldehyde-activated support method.
Figure 2B:
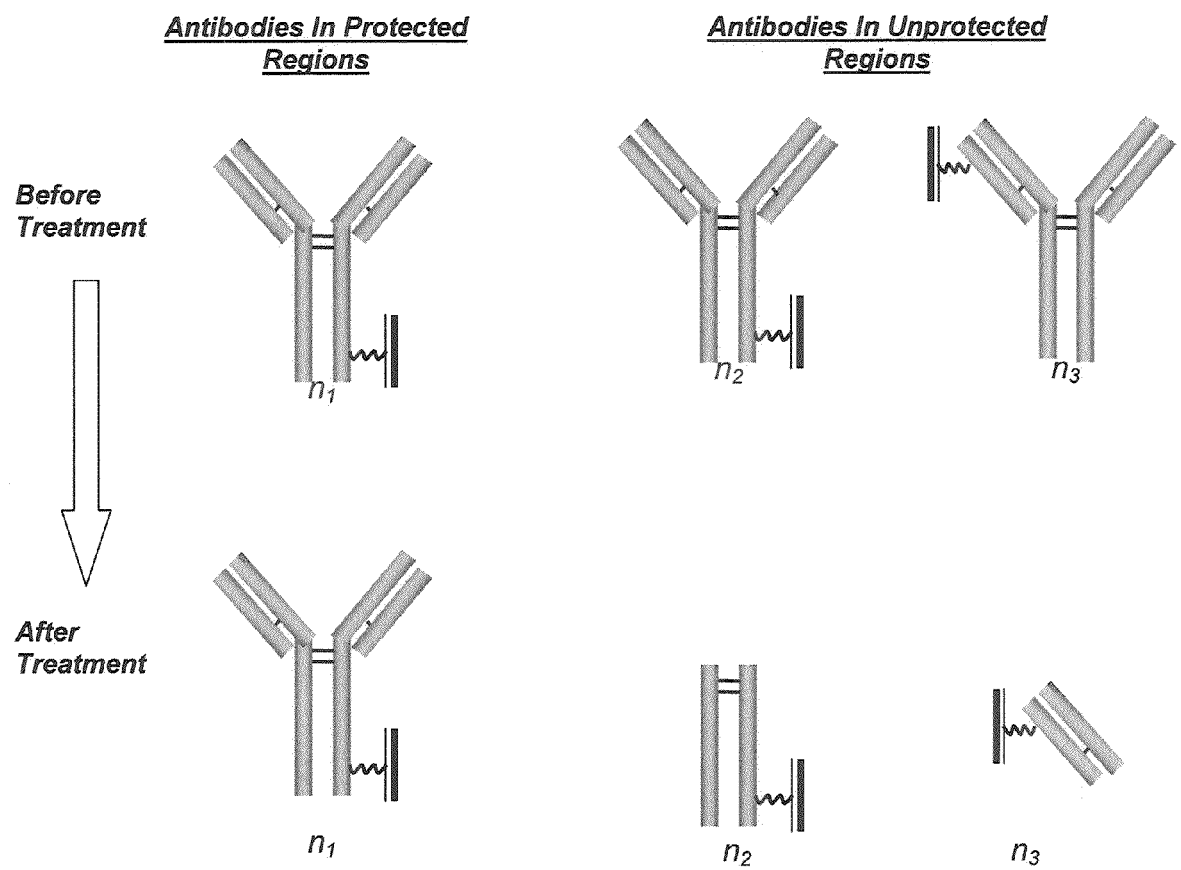
Figure 3:
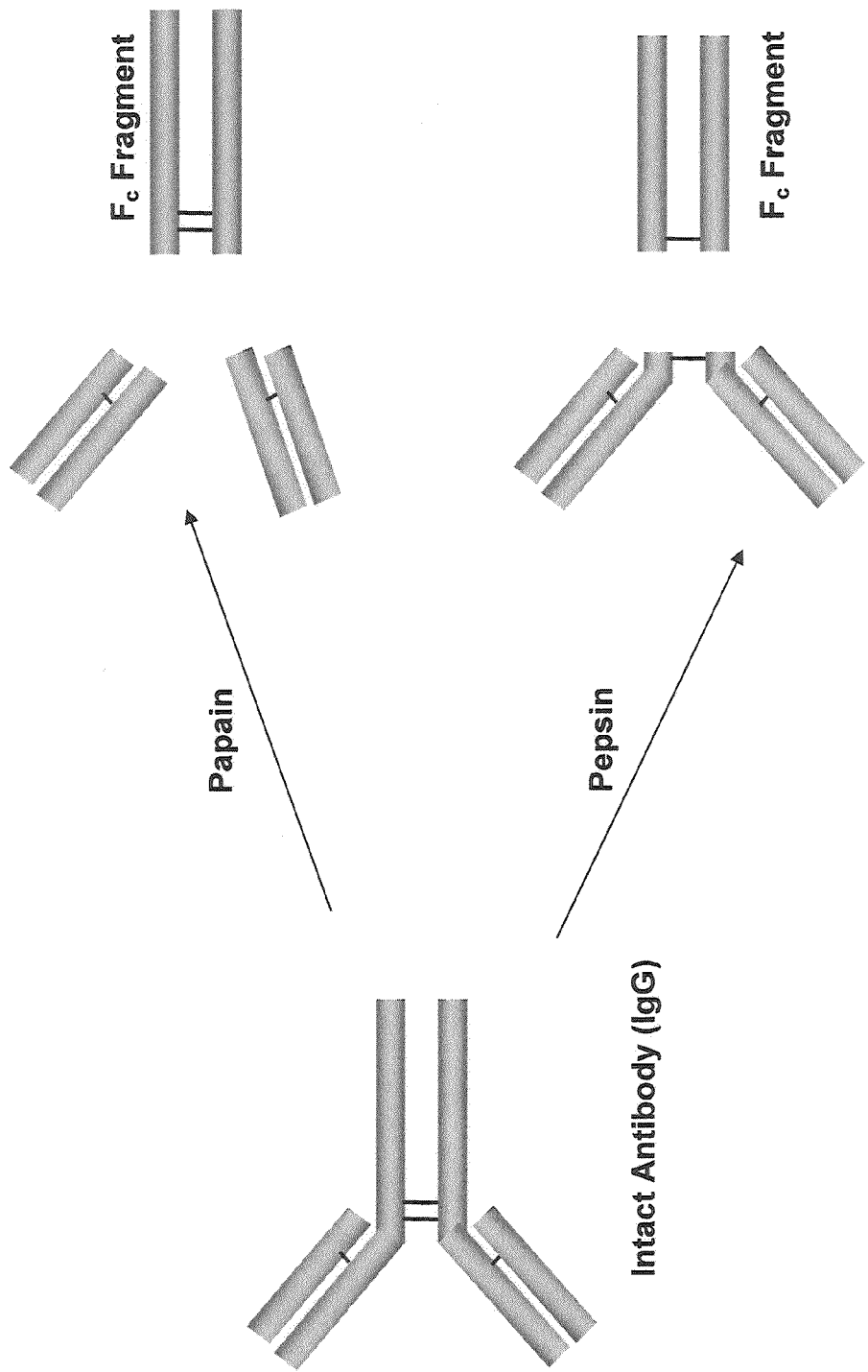
FIG. 3 is an illustration showing the structure of an IgG antibody before and after papain or pepsin treatment.

A ligand bound support obtained by any of the methods provided herein or elsewhere is treated with a size restricted cleaving agent to produce the restricted access media in which protected regions of the support contain uncleaved ligand binding agent molecule(s) and unprotected regions of the support contain cleaved ligand binding agent molecule(s). Without seeking to be limited by theory, some of the ligand binding agent molecule(s) within protected regions of the support will be inaccessible to the cleaving agent. This will leave ligand binding agent molecules residing in protected regions intact, while ligand binding agent molecules residing in unprotected regions of the support will be cleaved. For example, using an IgG antibody as the ligand binding agent molecule and an enzyme capable of cleaving away Fab regions as the cleaving agent, antibody molecules residing in unprotected regions are accessible to the enzyme and are cleaved. Antibodies residing in protected regions, however, are inaccessible to the enzyme and remain intact where they can function to bind their target molecule (see, FIGS. 1(a) and (b)). FIG. 2(b) is an illustration showing the structure of an IgG antibody covalently linked to an aldehyde-activated support using the Schiff base method before and after cleaving agent treatment. Antibody molecules residing within a protected region such as a pore remain intact following cleaving agent treatment. Antibody molecules residing in an unprotected region such as an outer surface, are cleaved. Depending on where the covalent linkage between the antibody molecule and the support occurs, either the $F_{ab}$ or $F_c$ sub-fragment remains covalently attached to the support following cleaving agent treatment. In FIG. 2(b), the cleaved sub-fragments representing the $F_{ab}$ and $F_c$ regions of the antibody form the blocking agent molecule(s). FIG. 2(a) is an illustration showing the structure of an IgG antibody covalently linked to a hydrazide-activated support before and after cleaving agent treatment. Antibody molecules residing within a protected region such as a pore remain intact following cleaving agent treatment. Antibody molecules residing in an unprotected region such as an outer surface, are cleaved. Because the antibody molecule is covalently linked to the hydrazide-activated support by the $F_c$ region, only the sub-fragment representing the $F_c$ region remains covalently linked to the support and forms the blocking agent molecule(s) in this illustration.

The size restricted cleaving agent can be a lyase or hydrolase. For example, the size restricted cleaving agent can be an enzyme or ribozyme. The size restricted cleaving agent can also be, for example, a protease (also referred to herein interchangeably with the term "peptidase"). Proteases that can be used include, but are not limited to, cysteine proteases, serine proteases, threonine proteases, aspartate proteases, and metalloproteases. Proteases that can be used as size restricted cleaving agents can also include, but are not limited to, trypsin, elastase, papain, pepsin, ficin, Lys-C, or Glu-C.

Several criteria can be considered when selecting the size restricted cleaving agent. In certain embodiments, a size restricted cleaving agent able to digest the ligand binding agent molecule at well-defined sites and that leaves the binding regions largely intact can be used. In certain embodiments, a size restricted cleaving agent that cleaves the ligand binding agent molecule into only a few large fragments can be used. The size restricted cleaving agent should also be large enough that it is excluded from the protected regions of the support such that ligand binding agent molecules residing in protected regions are not cleaved. The size restricted cleaving agent can be of similar size or larger than any proteins or molecules that are to be excluded from the protected region support.

Figure 5:
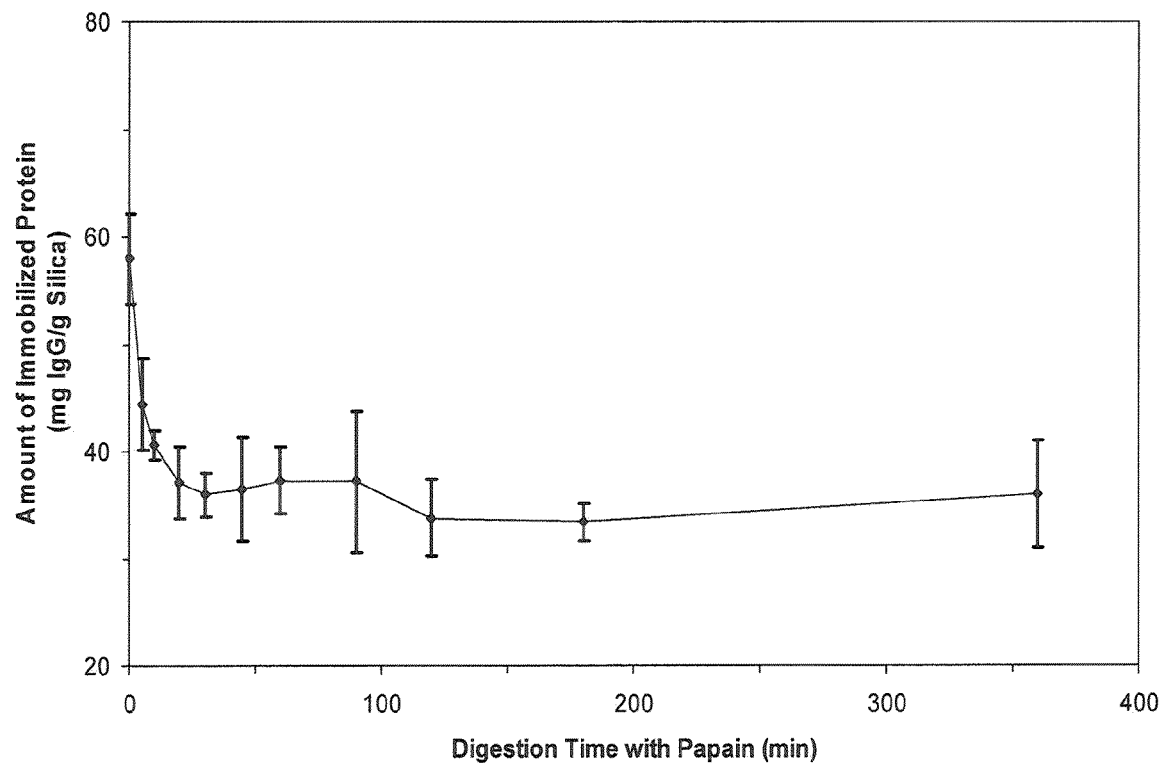
FIG. 5 is a line graph showing the amount of antibody remaining after cleaving agent treatment.

Activity of the size-restricted cleaving agent can also be modulated through control of a number of variables. Relevant variables that can be manipulated to control cleaving agent activity include, but are not limited to, temperature, pH, ionic strength, concentration of any required cations or anions, concentration of any required cofactors, time of treatment, and/or various combinations of these variables. Time of treatment with the size restricted cleaving agent can affect the amount of ligand binding agent molecules remaining on the support. For example, FIG. 5 shows the effect of time on the amount of antibody remaining after treatment using an antibody as the ligand binding agent molecule and papain as the size restricted cleaving agent.

To perform the cleavage treatment, the support is treated with a solution comprising a size restricted cleaving agent. The cleavage treatment can be stopped by removal of the cleavage agent and/or by addition of an inhibitor. Inhibitors can be cysteine protease inhibitors, serine protease inhibitors, threonine protease inhibitors, aspartic protease inhibitors, metalloprotease inhibitors. For example, iodoacetamide can be used to stop the cleavage treatment with papain. Soybean trypsin inhibitor, lima bean trypsin inhibitor, Kunitz inhibitor, serum trypsin inhibitor, and ovomucoid trypsin inhibitor, for example, can be used to stop the cleavage treatment with trypsin. Pepstatin can be used to stop the cleavage treatment with pepsin. Additional cleaving agent inhibitors will be readily recognized by those skilled in the art. The cleavage treatment can also be stopped by washing the support with phosphate buffered saline and water to remove the cleavage agent and any fragments of the ligand binding agent molecule that are cleaved from the support.

Figure 4A:
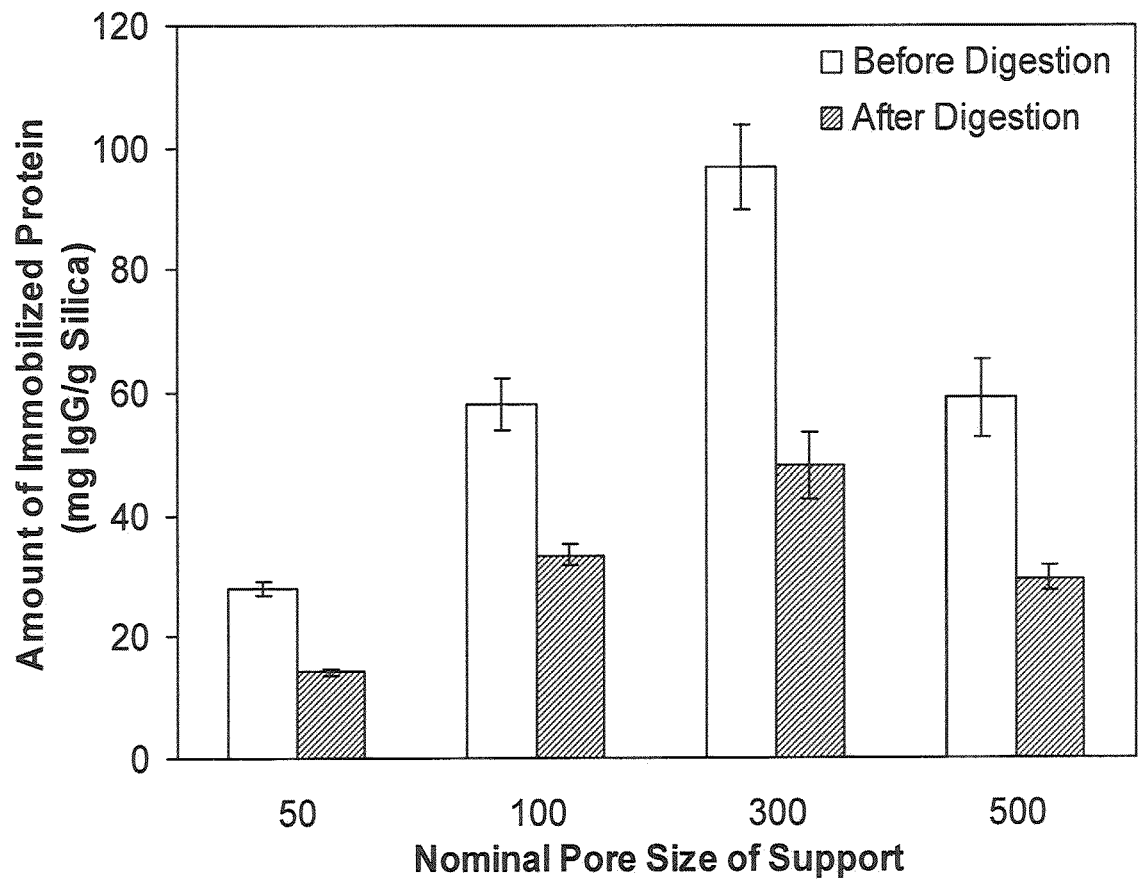
FIG. 4($a$) is bar graph showing the amount of covalently linked antibody versus nominal pore size of the support before and after cleaving agent treatment.
Figure 4B:
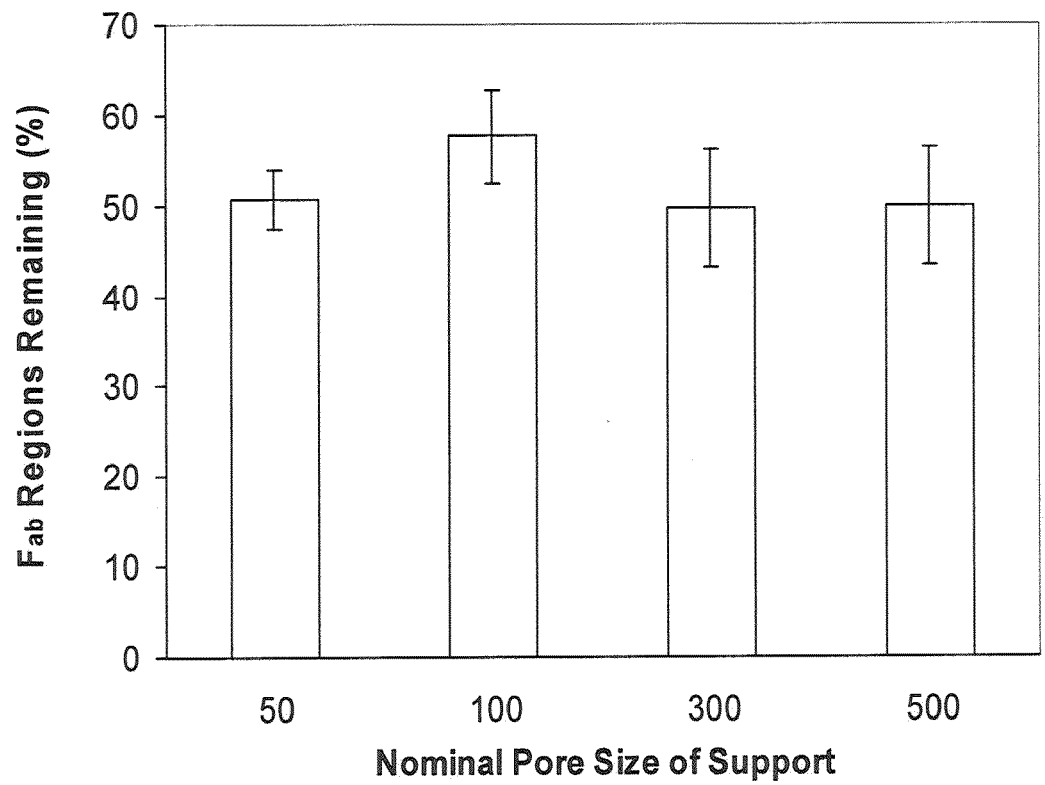

The size of the protected region can vary if exclusion of smaller or larger sample components is desired. When the ligand binding agent molecule is an IgG antibody, for example, the size of the protected region of the support can be about 50 Å to about 500 Å and preferably is about 100 Å to about 300 Å. FIG. 4 shows the effect of pore size on the total amount of covalently linked IgG using porous silica as the support. The total amount of bound IgG increased when pore size increased from 50 Å to 300 Å and decreased between 300 Å and 500 Å. FIG. 4(b) further indicates in examples using porous silica that pore size can affect accessibility by the cleaving agent.

The resulting RAM comprising protected covalently linked ligand binding agents can be used in a variety of applications that provide for target molecule purification or target molecule analysis. It is believed that this RAM comprising protected covalently linked ligand binding agents can be used for analytical chromatography, column chromatograph, batch chromatography, or biosensors.

Restricted Access Medium comprising Unbound Ligand Binding Agents or Enzymes in Protected Regions Other embodiments of the invention provided herein are restricted access media comprising a support wherein a plurality of protected regions of the support contain one or more unbound ligand binding agent(s) or enzyme molecules and wherein the ligand binding agent(s) or enzyme molecule(s) are retained in the protected regions by a capping agent. The protected region of the support can be on a surface, in a pore, or a combination of surfaces and pores. The support can be any support familiar to those skilled in the art that can be used directly or in a modified form for ligand binding agent attachment and combinations thereof. The support can be, for example, inorganic support materials. Inorganic support materials can be, for example, silica, glass, alumina, zirconia, silver, and gold. The support also can be biological support materials. Biological support materials can be, for example, agarose, dextran, and cellulose. The support further can be organic support materials and organic polymer supports. Organic support materials and organic polymer supports can be, for example, polystyrene, polymethacrylate, and polyamide. The support can be composite supports. Composite supports can be, for example, agarose coating on quartz, agarose coating on stainless steel, and coated polystyrene/divinylbenzene. Modified supports can be, for example, silica, glass beads, polystyrene, gold, or silver that contain, for example, surface diol groups, aldehyde groups, hydrazide groups, amine groups, and sulfhydryl groups. Formats for the support can comprise porous or non-porous particles, planar surfaces, or flow-through supports. Other formats for the support can include, but are not limited to, monolithic materials or perfusion supports, membrane supports, capillaries, fibers, and expanded bed supports. The unbound ligand binding agent can be a protein, a glycoprotein, a DNA, a RNA, a nucleoprotein, a carbohydrate-containing agent, a lipoprotein, or related agents. The DNA-based or RNA-based ligand binding agent can be an aptamer. Enzymes used in the RAM include, but are not limited to, glucose oxidase, horseradish peroxidase, and other enzymes that act on small substrates that can enter and leave the protected regions. Other enzymes used in the RAM can include, but are not limited to, that oxidoreductases, transferases, hydrolases, lyases, isomerases, and ligases. The capping agent can be a glycoprotein, a glycolipid, a carbohydrate-containing agent, or a combination of different capping agents. Related agents include, but are not limited to, a protein-protein complex, a protein-DNA complex, and a protein-RNA complex. Carbohydrate-containing agents include, but are not limited to, polysaccharides. Polysaccharides can include, but are not limited to, glycogen, dextran, agarose, and cellulose.

RAM provided herein thus comprise media where a ligand binding agent or enzyme is retained in a protected region in an unbound form. Without seeking to be limited by theory, RAM comprising unbound ligand binding agents or enzymes provide for presentation of the ligand binding agents or enzymes in a native or near-native form. In contrast, covalent linkage of a ligand binding agent to a support may decrease ligand binding agent activity and/or ligand binding agent specificity. Similarly, covalent linkage of an enzyme to a support may decrease enzymatic activity. Moreover, an unbound ligand binding agent or enzyme will respectively encounter a target molecule or substrate at a faster rate than a bound ligand binding agent or enzyme.

Method for Preparing Restricted Access Medium comprising Unbound Ligand Binding Agents or Enzymes in Protected Regions Various methods for preparing Restricted Access Medium comprising unbound ligand binding agents or enzymes in protected regions are provided herein. In certain embodiments, methods for preparing a restricted access media comprising incubating an activated support with a solution comprising i) a ligand binding agent or an enzyme molecule and ii) an activated capping agent; and removing unbound capping agent from the incubated support, thereby preparing the restricted access media comprising a support wherein a plurality of protected regions of the support contain one or more unbound ligand binding agent(s) or enzyme molecule(s) and wherein the ligand binding agent(s) or enzyme molecule(s) are retained in the protected regions by the capping agent are provided.

Methods provided herein can further comprise washing the restricted access media with a solution to deactivate bound capping agent. Solutions to deactivate bound capping agent include, but are not limited to, a hydrazide-containing agent, an amine-containing agent, and a hydrazine-containing agent. For example, the hydrazide-containing agent or amine-containing agent can be oxalic dihydrazide adipic dihydrazide, succinic dihydrazide, ethanolamine, and ethylamine.

The activated support can be any support that can be used directly or in a modified form for ligand binding agent attachment and combinations thereof. In certain embodiments, activated supports can comprise inorganic support materials. Inorganic support materials can include, but are not limited to, silica, glass, alumina, zirconia, silver, and gold. In certain embodiments, activated supports can comprise biological support materials. Biological support materials can include, but are not limited to, agarose, dextran, and cellulose. Activated supports can comprise one or more organic support material(s) and organic polymer supports. Organic support materials and organic polymer supports can include, but are not limited to, polystyrene, polymethacrylate, and/or polyamide. In other embodiments, the activated support can comprise composite supports. Composite supports include, but are not limited to, an agarose coating on quartz, an agarose coating on stainless steel, and coated polystyrene/divinylbenzene. In other embodiments, the activated support can comprise modified supports. Modified supports can include, but are not limited to, silica, glass beads, polystyrene, gold, or silver that contain an added chemical group. Chemical groups used in modified supports include, but are not limited to, surface diol groups, aldehyde groups, hydrazide groups, amine groups, and sulfhydryl groups. The hydrazide group, an amine group, an aldehyde group, or a combination of hydrazide groups, amine groups, and/or aldehyde groups of the activated support can be activated to permit covalent binding of a ligand binding agent or linking agent.

The unbound ligand binding agent or enzyme molecule can be a protein, a glycoprotein, a DNA, a RNA, a nucleoprotein, a carbohydrate containing agent, a lipoprotein, or related agents. Related agents include, but are not limited to, a protein-protein complex, a protein-DNA complex, and a protein-RNA complex. The unbound ligand binding agent or enzyme molecule and activated capping agent can be incubated together or separately with the activated support.

The activated capping agent can be a glycoprotein, a glycolipid, or a carbohydrate-containing agent. Carbohydrate-containing agents include, but are not limited to, polysaccharides. Polysaccharides include, but are not limited to, glycogen, dextran, agarose, and cellulose. The activated capping agent can be activated by oxidization with an oxidizing agent. Oxidizing agents can include, but are not limited to, periodate, a periodate-related chemical, or an enzyme treatment. The periodate can include, but is not limited to, sodium periodate, potassium periodate, or periodic acid. The activated capping agent can be an oxidized capping agent. For example, the oxidized capping agent can be an oxidized glycoprotein, a oxidized glycolipid, or an oxidized carbohydrate-containing agent. Oxidized carbohydrate-containing agents include, but are not limited to, oxidized glycogen, oxidized dextran, oxidized agarose, or oxidized cellulose.

Figure 9:
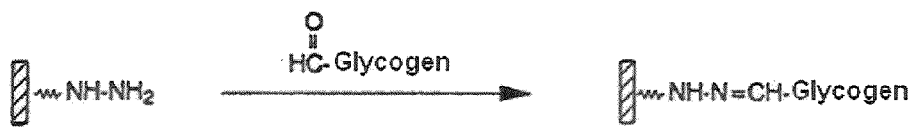
FIG. 9 is an illustration showing (a) reaction between oxidized glycogen as the capping agent and a hydrazide-activated support and (b) retention of a protein as oxidized glycogen as the capping agent reacts with the hydrazide-activated support.
Figure 9:
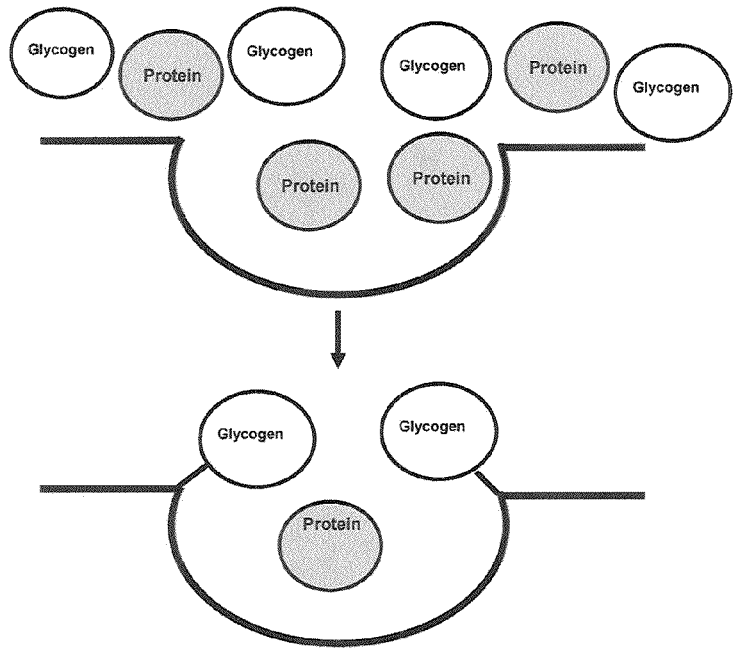

Without seeking to be limited by theory, when the oxidized capping agent is incubated with the activated support, groups of the oxidized capping agent such as aldehyde groups, form covalent bonds with groups of the support such as hydrazide groups. Thus, the capping agent retains the ligand binding agent or enzyme molecule(s) present in the reaction mixture. FIG. 9 is an illustration showing retention of a protein using oxidized glycogen as the capping agent and a hydrazide-activated support.

After retaining the ligand binding agent or enzyme molecule(s), the resulting restricted access media can be used for measuring the activity of the retained ligand binding agent or enzyme molecule(s) and/or placed into columns for uses such as high performance affinity chromatography, solid-phase immunoassays, and immobilized enzyme reactors.

The resulting RAM comprising protected unbound ligand binding agents can be used in a variety of applications that provide for target molecule purification or target molecule analysis. It is believed that this RAM comprising protected unbound ligand binding agents can be used for analytical chromatography, column chromatography, batch chromatography, or biosensors.

The resulting RAM comprising protected unbound enzymes can be used in a variety of applications that provide for conversion of substrates to products. These applications of RAM comprising protected unbound enzymes include both analytic and preparative uses. It is anticipated that this RAM comprising protected unbound enzymes are especially useful in applications where it is desirable to sequester the enzyme from the sample containing the substrate.

Kits for Preparing a Restricted Access Media

Other embodiments of the invention are kits for preparing a restricted access media comprising: i) a support that is substantially free of ligand binding agent molecules and ii) a size restricted cleaving agent. The kits can further comprise instructions for using the kit. The kits can also comprise an activated support or an unactivated support. The kits can also comprise a solution for activating the support. The kits can further comprise a ligand binding agent, a linking agent, and/or an enzyme molecule that is not covalently linked to the support. The restricted access media that is prepared using the kits can comprise a support wherein a plurality of protected regions of the support contain one or more covalently linked ligand binding agent molecules and wherein a plurality of unprotected regions of the support contain one or more covalently linked blocking agent molecule(s).

In other embodiments, kits comprising a restricted access media comprising: i) a support wherein a plurality of protected regions of the support contain one or more covalently linked ligand binding agent molecules and wherein a plurality of unprotected regions of the support contain one or more covalently linked blocking agent molecule(s) and ii) at least one container are provided. The kits can further comprise instructions for using the kit.

In still other embodiments of the invention, kits for preparing a restricted access media comprising: i) a support that is substantially free of ligand binding agent or enzyme molecules, and ii) a capping agent are provided. The kits can further comprise a solution for activating the capping agent. The kits can further comprise a solution for activating the support. The kits can further comprise instructions for their use. The kits can comprise an activated support. The kits can further comprise a ligand binding agent or an enzyme molecule that is not associated with the support. Restricted access media that is prepared from the kit can comprise a support wherein a plurality of protected regions of the support contain one or more unbound ligand binding agent(s) or enzyme molecule(s) and wherein the ligand binding agent(s) or enzyme molecule(s) are retained in the protected regions by a capping agent.

Other embodiments of the invention are kits comprising a restricted access media comprising: i) a support wherein a plurality of protected regions of the support contain one or more unbound ligand binding agent or enzyme molecules and wherein the ligand binding agent(s) or enzyme molecules are retained in the protected regions by a capping agent, and ii) at least one container. The kits can further comprise instructions for using the kit.

EXAMPLES

The following examples describe embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

Example 1

Description of Chemicals and Apparatus

Nucleosil Si-50, Si-100, Si-300 and Si-500 silica supports (7 μm particle diameter; nominal pore size, 50, 100, 300 or 500 Å, respectively) were from Macherey Nagel (Düren, Germany). Rabbit immunoglobulin G (IgG, reagent grade), monoclonal anti-fluorescein antibodies (anti-FITC clone FL-D6, produced in mouse ascites fluid), the fluorescein conjugate of bovine serum albumin (fluorescein-BSA; prepared using fluorescein isothiocyanate and giving 12 mol fluorescein/mol protein), papain (85% protein, from papaya latex), fluorescein ($\geq$90% pure), periodic acid reagent (>99% pure), sodium cyanoborohydride (>99% pure), sodium borohydride (98% pure), D/L-dithiothreitol (DTT, >99% pure), iodoacetamide (~99% pure), and ethylenediaminetetraacetic acid disodium salt dehydrate (EDTA, ~99% pure) were from Sigma (St. Louis, Mo.). The 3-glycidoxypropyltrimethoxysilane (>94% pure), and oxalic dihydrazide (98% pure) were from Aldrich (Milwaukee, Wis.). Ethylene glycol (>99% pure) was from Fisher Scientific (Pittsburgh, Pa.). The acetic acid (>99.7% pure) was from EMD chemicals (Gibbstown, N.J.). Reagents for the bicinchoninic acid (BCA) protein assay were from Pierce (Rockford, Ill.). All aqueous solutions were prepared using water from a Nanopure system (Barnstead, Dubuque, Iowa) and were filtered using 0.22 μm nylon filters (Fisher Scientific).

Slide-A-Lyzer dialysis cassettes (7 kDa MW cutoff, 0.5-3 mL capacity) were from Pierce. BCA assays were performed using a Shimadzu UV-160A spectrophotometer (Kyoto, Japan). Fluorescence spectra were acquired with a Shimadzu RF-5301PC spectrofluorometer using the following settings: excitation wavelength, 460 nm; emission wavelengths, 300-700 nm; slit width, 3.0 nm for both excitation and emission; scan speed, medium; sensitivity, high. The buffers employed in preparing samples were used to autozero the spectrofluorometer before each analysis.

The RAM prepared using IgG antibody as the ligand binding agent molecule and control columns were packed using a Shimadzu LC-10AT pump and a Rheodyne 710 six-port valve (Cotati, Calif.). The chromatographic system comprised a Perkin Elmer Series 200 micropump (Norfolk, Conn.) and a Shimadzu RF-525 fluorescence detector. Samples were injected using a Rheodyne LabPro valve equipped with a 200 μL loop. Chromatographic data were collected and processed using LabView 5.1 (National Instruments, Austin, Tex.).

Example 2

Preparation of Aldehyde-Activated Support

A silica support was converted into a diol form by treating a 500 mg quantity of the support with 3-glycidoxypropyltrimethoxysilane to introduce epoxy groups onto the silica. The resulting epoxy silica support was treated with 0.1 M sodium acetate buffer at pH 5.5 by sonication under vacuum for 10-15 minutes. 3-Glycidoxypropyltrimethoxysilane (5%-10% v/v) was added into the suspension and shaken for 5 hours at 90° C. The epoxy silica support was washed several times with water and an aqueous solution of sulfuric acid (pH 3.0). The epoxy silica support was then suspended in 100-150 mL of an aqueous sulfuric acid solution (pH 3.0) and refluxed for one hour to convert the epoxy silica support into a diol form. The resulting diol silica support was washed with several portions of water, methanol and ether. The diol silica support was dried overnight under vacuum and stored in a desiccator until use. The diol content of the diol silica support was determined using an iodometric capillary electrophoresis assay.

To convert the diol groups to aldehyde groups, 500 mg of the diol silica support was suspended in 10 mL of a 90% (v/v) mixture of acetic acid and water that contained 500 mg periodic acid. The mixture was sonicated under vacuum for 20 minutes and shaken on a wrist-action shaker for 2 hours at room temperature. The resulting aldehyde-activated silica was washed several times with water and, 0.10 M potassium phosphate buffer (pH 6.0). The aldehyde-activated silica support was used directly for preparing a restricted access media or for preparing a hydrazide-activated silica support.

Example 3

Preparation of Hydrazide-Activated Support

To prepare a hydrazide-activated silica support, 200 mg of the aldehyde-activated silica support was suspended in 30 mL of 0.10 M potassium phosphate buffer (pH 5.0) that contained a 5-fold mole excess of oxalic dihydrazide versus the initial diol groups present in the added aldehyde-activated silica support. The slurry was shaken for 2 hours at room temperature on a wrist-action shaker. The support was then washed several times with 0.10 M potassium phosphate buffer (pH 7.0). After activation, a 25-fold mol excess of sodium borohydride (versus the initial diol groups) in 4 mL of 0.10 M potassium phosphate buffer (pH 8.0) was added in several small portions to the support slurry to reduce any remaining aldehyde groups. This mixture was shaken for 90 minutes at room temperature and washed several times with 0.10 M potassium phosphate buffer (pH 7.0). The final hydrazide-activated support was stored in 0.10 M potassium phosphate buffer (pH 7.0) at 4° C. until use.

Example 4

Preparation of RAM Using IgG Antibody Covalently Linked According to an Aldehyde-Activation (Schiff Base) Method Rabbit IgG was used without pretreatment. A 13 mg/mL slurry of aldehyde-activated silica (prepared as described in Example 2) was sonicated under vacuum for 5 minutes in 0.10 M potassium phosphate buffer (pH 6.0). To this slurry was added 0.69, 0.69, 0.20 or 0.069 mg antibody per mg of aldehyde-activated Nucleosil Si-50, Si-100, Si-300 or Si-500 silica, respectively. Rabbit IgG amounts were at least two-fold greater than the maximum amount that could be immobilized to the surface of each support, as determined by Kim et al., (In *Handbook of Affinity Chromatography*, Hage, D. S., ed. CRC Press: Boca Raton, Fla. (2006)) and calculations based on the known surface area of these supports and the size of IgG (see, Walters et al. (140 *Anal. Biochem.* 190-195 (1984)). About 8 mg/mL sodium cyanoborohydride was also added to each reaction slurry to promote the formation of stable secondary amine linkages between the retained antibodies and the support. The slurry was shaken for 3 days at 4° C. The resulting material was washed several times with 0.10 M potassium phosphate buffer (pH 8.0). The support was then suspended in 2 mL of a 4 mg/mL solution of sodium borohydride in 0.10 M potassium phosphate buffer pH (8.0) to convert any remaining aldehyde groups into alcohols. The mixture was shaken for 90 minutes at room temperature. The resulting antibody restricted access medium was washed several times with water for later use in a BCA assay or dried overnight under vacuum and stored in a desiccator for later analysis.

Example 5

Preparation of RAM Using IgG and Anti-Fluorescein Antibodies Covalently Linked According to a Hydrazide-Activation (Site-Selective) Method Rabbit IgG and anti-fluorescein (monoclonal anti-FITC clone FL-D6) antibodies to be covalently linked using the hydrazide-activation method were oxidized with periodate to generate aldehyde groups in their carbohydrate regions. To oxidize rabbit IgG, 2 mg/mL of rabbit IgG was added to a solution containing 20 mM sodium acetate and 0.15 M sodium chloride (pH 5.5). To oxidize anti-fluorescein antibodies, the anti-fluorescein antibodies were exchanged into 20 mM sodium acetate and 0.15 M sodium chloride (pH 5.5) buffer using Econo-Pac 10 DG desalting columns (BioRad; Hercules, Calif.) at about 2 mg/mL final concentration. A 20 mM solution of periodic acid was made in the same buffer (20 mM sodium acetate containing 0.15 M sodium chloride, pH 5.5) and added to the antibody solutions in a 1:1 volume ratio. The mixtures were protected from light exposure by wrapping the containers in aluminum foil and shaken for 30 minutes at room temperature. The oxidation process was quenched by adding 0.25 mL of ethylene glycol per mL of the oxidized antibody solution and shaking an additional 5 minutes at room temperature. Excess periodic acid was removed from the oxidized antibody solution by dialysis in two hour cycles against one 2 L portion of 20 mM sodium acetate and 0.15 M sodium chloride (pH 5.5) and three 2 L portions of 0.10 potassium phosphate buffer (pH 7.0). The final oxidized antibody solution was passed through a 0.22 µm filter to remove any cross-linked or precipitated immunoglobulins. The concentrations of the final antibody solutions were determined to be 0.6-0.7 mg/mL by a BCA assay. Oxidized antibody was combined with 4-5 mg hydrazide-activated silica supporting antibody and incubated in 0.10 M potassium phosphate buffer (pH 7.0) at 4° C. for 3 days. The supernatant was collected and analyzed by a BCA assay. The support containing the covalently linked antibody was packed within a column or washed several times with water and dried overnight under vacuum for analysis by a BCA assay.

Example 6

Preparation of Immunoaffinity-Restricted Access Media

RAM prepared in Examples 4 and 5 were treated with a size restricted cleaving agent to prepare immunoaffinity restricted access media ("IA-RAM"). In this example, papain was used as the size restricted cleaving agent. The papain solution comprised 2 mg/mL papain in phosphate-buffered saline (PBS; pH 7.5) containing 50 mM phosphate, 150 mM sodium chloride, 2.7 mM potassium chloride, 2 mM EDTA and 1 mM DTT. DTT was used to reduce disulfide bonds within papain for activation.

To perform the papain cleavage treatment, the desired immunoaffinity support (either aldehyde-activation method or hydrazide-activation method) was washed twice with the PBS (pH 7.5), suspended in PBS (pH 7.5) and sonicated for 5 minutes. The concentration of antibodies in the solution was 0.3-1.2 mg/mL. The papain solution was added to the slurry at a papain:immunoglobulin ratio of 1:100 (w/w). The mixture was incubated at 37° C. for 30 minutes. The papain treatment was stopped by adding 30 mM iodoacetamide and incubating in the dark for 60 minutes on ice. The papain-treated support was washed several times with PBS and water to remove the papain and any antibody fragments cleaved from the support. Supports to be examined by a BCA assay were dried overnight under vacuum and stored in a desiccator at room temperature. The anti-fluorescein support to be used in chromatographic studies was washed three times with 0.10 M potassium phosphate buffer (pH 7.4) and stored in this buffer at 4° C. until use.

The anti-fluorescein IA-RAM support was packed into a sandwich microcolumn according to Clark et al., (73 *Anal. Chem.* 2157-2164 (2001)) and Clarke et al., (73 *Anal. Chem.* 1366-1373 (2001)). The column had an inner diameter of 2.1 mm and a total length of 1.0 cm, with a 2 mm long section in the middle containing the anti-fluorescein IA-RAM support while the remainder contained an inert layer of diol silica. The support was placed into the column by making fifty-three 200-µL injections of a 0.32 mg/mL slurry of the anti-fluorescein IA-RAM support in 0.067 M potassium phosphate buffer (pH 7.0). A 2 mg/mL slurry of diol Nucleosil Si-100 in 0.067 M potassium phosphate buffer (pH 7.0) was used to fill the remainder of the column. A control column was prepared in a similar manner using diol silica in place of the IA-RAM support.

Example 7

Evaluation of IA-RAM Supports

The amount of polypeptides on an IA-RAM support before or after treatment with papain was determined using a BCA assay. The amount of antibodies/IgG placed on a support by the hydrazide-activation (site-selective) method was determined by comparing the final and initial concentrations of the antibodies/IgG in the supernatant of the reaction slurry and/or by directly measuring the final protein content of the support. The amount of antibodies/IgG remaining after papain treatment was determined by comparing the protein content of the support before and after papain treatment.

The binding properties of the anti-fluorescein IA-RAM support were initially determined before and after digestion by reacting this support with a known excess of fluorescein (sodium salt, MW=376 Da) or fluorescein-BSA conjugate (average MW=69.5 kDa). Studies were performed using anti-fluorescein antibodies covalently linked to Nucleosil Si-100 using the hydrazide-activation method. A 2 mg portion of the desired anti-fluorescein support was incubated with shaking in 1 mL of a 0.040 μg/mL fluorescein solution or 1 mL of 20 μg/mL fluorescein-BSA solution in 0.1 M potassium phosphate buffer (pH 7.4) at 4° C. for 30 minutes. The mixtures were centrifuged and the supernatant was analyzed for fluorescein or fluorescein-BSA content based on the fluorescence of the solutions. Standard solutions that contained 0.002-2.0 μg/mL fluorescein or 1-30 μg/mL of the fluorescein-BSA conjugate in 0.10 M potassium phosphate buffer (pH 7.4) were also analyzed. The amount of fluorescein or fluorescein-BSA bound to the anti-fluorescein IA-RAM supports was determined by comparing the final and initial concentrations of fluorescein or fluorescein-BSA that remained in solution.

For chromatographic studies, 200 μL injections of samples containing 0.5 nM fluorescein or 3 nM of fluorescein-BSA were made at flow rates ranging from 0.1-1.0 mL/min. The injections were performed at room temperature using 0.067 M potassium phosphate buffer (pH 7.4) as the application buffer. Two or three replicate injections were made at each flow rate onto columns containing the anti-fluorescein IA-RAM support or the corresponding control support. The amount of non-retained fluorescein or fluorescein-BSA was monitored using an on-line fluorescence detector set at excitation and emission wavelengths of 488 and 520 nm, respectively. The fraction of extracted fluorescein was calculated by comparing the areas of the non-retained peaks to those obtained using a control column. Measurements made at 0.01 mL/min (i.e., an incubation time 10-fold longer than the longest sample contact time used in the extraction study) were used to correct the peak areas for any small amount of non-binding, fluorescent contaminants that were present in the samples. The retained species were eluted between studies by washing the column with a 0.067 M potassium phosphate buffer (pH 2.5) for 20 minutes. Elution was followed by a column regeneration step by applying 0.067 M phosphate application buffer (pH 7.4) for 10 minutes before each new sample injection.

Example 8

Effect of Cleaving Agent Treatment Time

FIG. 5 shows the results of varying the treatment time of the cleaving agent. Rabbit IgG was covalently linked according to the aldehyde-activation (i.e., Schiff base) method onto a 100 Å pore size silica support and treated with papain as the cleaving agent. Antibodies covalently linked to this support were treated using an initial papain:antibody ratio of 1:100 (w/w), but the treatment time ranged from 0 to 6 hours.

As shown in FIG. 5, a sharp decrease in the amount of antibody remained on the support as the treatment time with papain increased from 0 to 30 minutes. At 30 minutes, the total antibody content had decreased to 36 (±2) mg/g support, which was 62 (±6)% of the antibody content before treatment. As the treatment time continued, however, the amount of antibody remaining on the support decreased only slightly and approached a fixed value. These results indicate that all of the accessible antibodies on the support had been cleaved by papain. Similar results were observed in experiments using 300 Å pore size silica supports.

Example 9

Effect of Cleaving Agent Concentration

The concentration of cleaving agent added to the support for treatment (as reflected by the cleaving agent:antibody ratio) can also control the amount of $F_{ab}$ regions remaining on the IA-RAM support after cleaving agent treatment. Without being held to a particular theory, a low concentration of cleaving agent may lead to slow or incomplete digestion of antibodies while higher concentrations may lead to aggregation or adsorption onto the support. The effect of varying cleaving agent:antibody ratio was examined using rabbit IgG that was covalently linked using the hydrazide-activated support method onto a 100 Å pore size silica support and treated with papain for 3 hours. In this study the concentration of papain used for digestion was varied from a papain:antibody ratio of 1:400 to 1:10 (w/w).

Figure 6:
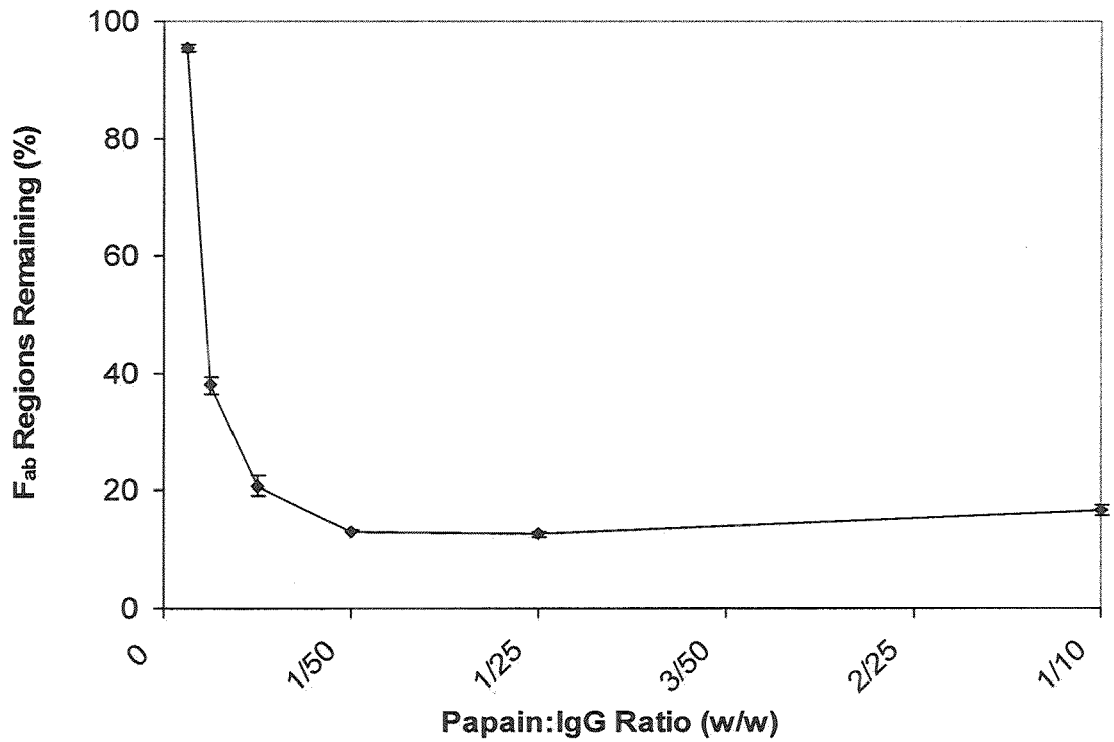
FIG. 6 is a line graph showing the effect of cleaving agent concentration on the amount of $F_{ab}$ and antibody remaining following treatment with cleaving agent.
Figure 6:
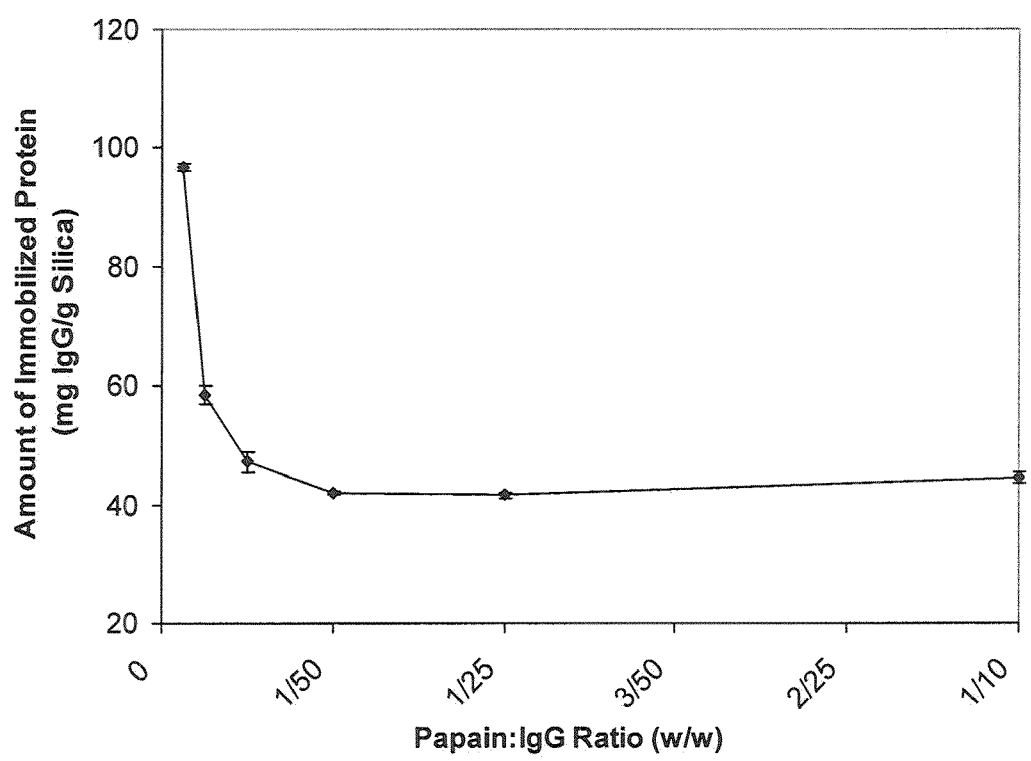

FIG. 6 shows a sharp decrease in the amount of antibody left on IA-RAM supports after treatment with papain using papain:antibody ratios of 1:400 to 1:100, or 0.0025 to 0.010 papain:IgG (w/w). Similar antibody contents were observed after treatment of supports using larger papain:antibody ratios of 1:50-1:10, or 0.020-0.10 papain:IgG (w/w). Therefore, most of the accessible antibodies were cleaved by papain within 3 hours using an papain:antibody ratio of 1:100 or greater.

Example 10

Effect of Method for Covalently Linking IgG Antibody

The effect of the method for covalently linking the antibody was examined by covalently linking rabbit IgG using an aldehyde-activated silica support (Schiff base) method or a hydrazide-activated silica support method. Supports with a pore size of 100 Å were treated with papain for 3 hours using an papain:antibody ratio of 1:100. In the aldehyde-activated silica support (Schiff base) method, the polypeptide content of the support before and after treatment with papain was 58 (±4) or 33 (±2) mg/g silica, respectively.

In the hydrazide-activated support method, the polypeptide content of the support before and after treatment with papain was 98 (±4) and 47 (±2) mg/g silica, respectively. The original amount of covalently linked antibodies following the hydrazide-activated support method was 1.6-fold larger than that obtained by the aldehyde-activated silica support (Schiff base) method, while the amount of antibodies remaining after treatment with papain was 1.4-fold larger. The larger amount of covalently linked antibodies in the hydrazide-activated support method compared to the aldehyde-activated silica support (Schiff base) method has been observed and may be related to the more uniform orientation of antibodies in the hydrazide-activated support method. (See e.g., Clarke et al., (888 *J. Chromatog.* 13-22 (2000)). This difference compared to the aldehyde-activated silica support (Schiff base) method may also reflect the more ordered orientation of antibodies in the hydrazide-activated support method, which could have made more $F_{ab}$ regions accessible to papain for cleavage. Without being limited by theory, however, these results may vary with the type of antibody used. For example, anti-fluorescein mouse monoclonal antibodies retained by the hydrazide-activated support method gave a 53% recovery of activity after treatment with papain, which is similar to the results noted in this section for rabbit IgG when using the aldehyde-activated silica support (Schiff base) method. Thus, the method of covalently linking the antibody may affect the preparation of the RAM.

The overall binding capacity of the support may further depend on the activity of the covalently linked antibodies along with the total antibody content and fraction of $F_{ab}$ regions present on the final material. For example, if there is about a 50% retention of activity for $F_{ab}$ regions in the aldehyde-activated silica support (Schiff base) method, the resulting binding capacity for a RAM can be about 110 nmol/g silica for a low mass target. If 85-100% retention of activity occurs in the hydrazide-activated support method, the resulting binding capacity for a RAM can be about 104-122 nmol/g silica for a low mass target even though fewer $F_{ab}$ regions are present in the final material. Therefore, slightly different values may be obtained for other types of antibodies or when using alternative methods for covalently linking the ligand binding agent molecule.

Example 11

RAM in Static Binding

Fluorescein and a fluorescein-BSA conjugate were used as low mass and high mass target to evaluate the binding and selectivity of a RAM prepared using covalently linked anti-fluorescein antibodies. Fluorescein was useful as a model for drugs or other low mass solutes because of its size (MW, 376 Da), its ease of detection, and the availability of monoclonal anti-fluorescein antibodies. Fluorescein-BSA (MW, 69.5 kDa) was valuable as a model for a high mass target because both BSA and its human counterpart HSA (MW, 66.5 kDa) bind to a variety of drugs, hormones and other small solutes.

Anti-fluorescein antibodies were covalently linked to a silica support with a pore size of 100 Å by the hydrazide-activated support method. A portion of this support was set aside for use as a reference while the remainder was treated with papain for 90 minutes at 37° C. using an cleaving agent: antibody ratio of 1:100 (w/w). The resulting RAM was washed with PBS buffer to remove the cleaving agent and any $F_{ab}$ fragments cleaved from the antibodies. Known amounts of the treated and original anti-fluorescein RAM were incubated for 30 minutes with an excess of fluorescein or fluorescein-BSA conjugate to saturate any accessible binding regions for these targets on the support. The fluorescein or fluorescein-BSA that was bound by anti-fluorescein antibodies was determined by determining the amount of the analytes that remained in solution after the incubation step.

The original binding capacity of the covalently linked antibodies was estimated using this approach to be 0.97 (±0.02) µg/g silica for fluorescein or 0.69 (±0.01) mg/g silica for the fluorescein-BSA conjugate. It was also found that the binding capacity for fluorescein-BSA decreased by 92% (±3)% for the anti-fluorescein support after treatment with papain. However, the binding capacity for fluorescein decreased by only 47 (±2)%. These results indicated that the treated support was more selective in binding to a low mass target such as fluorescein and gained some size selectivity, as would be predicted for a RAM material.

Example 12

RAM for Ultrafast Extraction

The RAM, specifically an IA-RAM made using anti-fluorescein antibody, was tested for use in a flow-based system for the selective, ultrafast extraction of fluorescein versus a fluorescein-BSA conjugate. This was accomplished by comparing the results obtained with a RAM column to results for a control column containing only diol silica. The amount of injected fluorescein or fluorescein-BSA in these studies was 1.5% or 20% of the total binding capacity for these two analytes on the RAM support.

Figure 7:
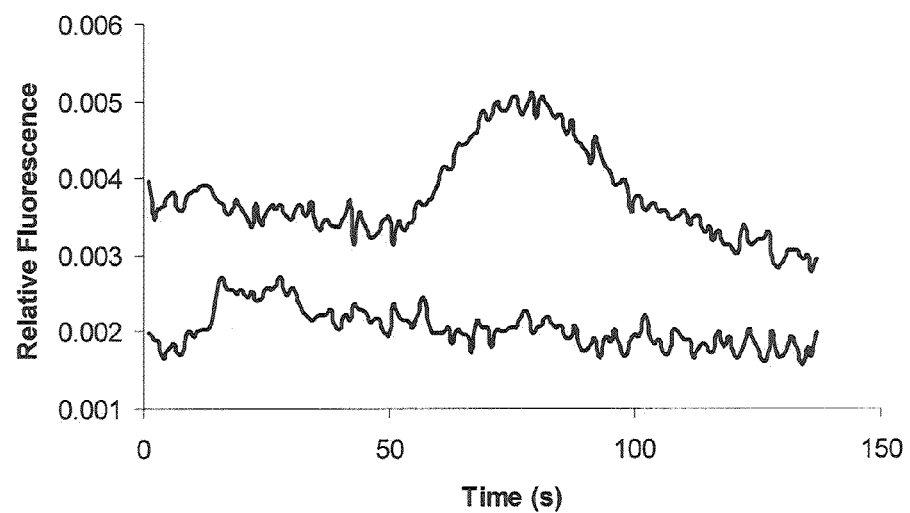
FIG. 7 are chromatograms showing (a) fluorescein retention by an anti-fluorescein RAM column and a control column and (b) fluorescein-bovine serum albumin (BSA) retention by an anti-fluorescein RAM column and a control column.
Figure 7:
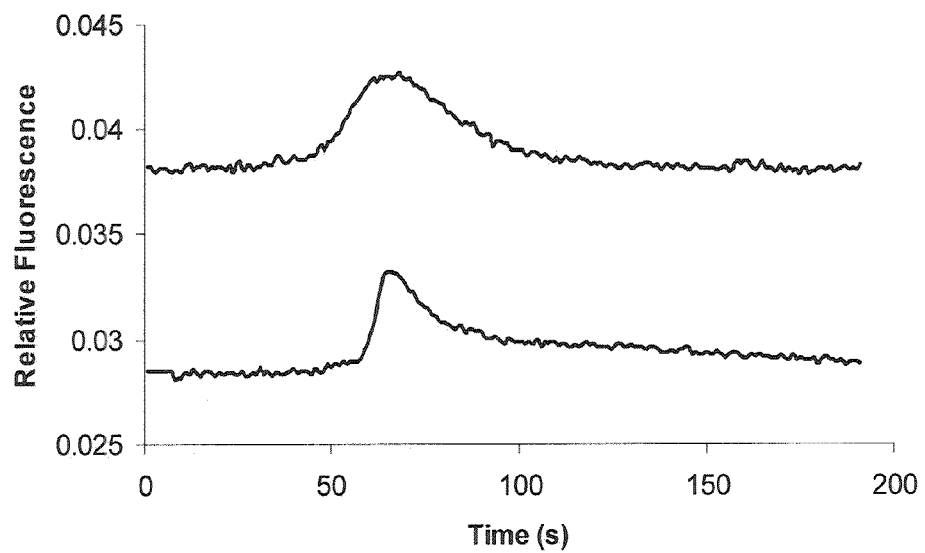

FIGS. 7(*a*) and (*b*) show chromatograms obtained when fluorescein or fluorescein-BSA were injected at 0.1 mL/min onto the anti-fluorescein RAM column and a control column with no antibodies present. The fluorescein was quantitatively extracted by the RAM column but gave no signs of retention on the control column under the same conditions. When the same experiment was performed with fluorescein-BSA, no significant degree of binding was seen on either the RAM column or control column.

Figure 8:
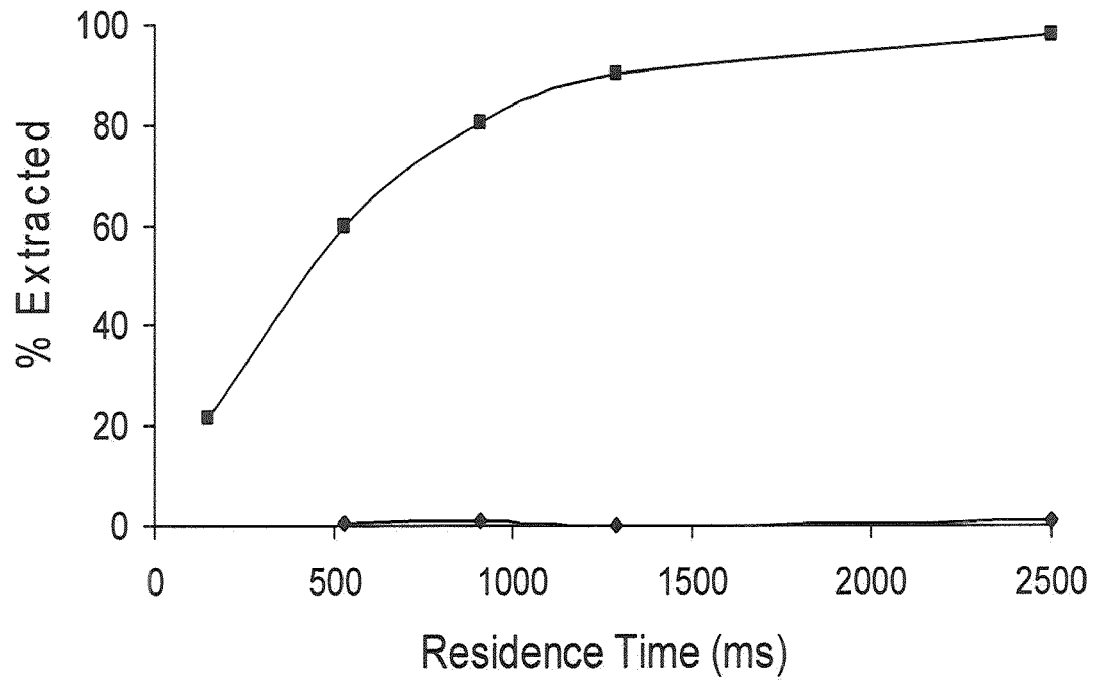
FIG. 8 shows the percent extraction of fluorescein or fluorescein-BSA by an anti-fluorescein RAM.

FIG. 8 illustrates how the extent of extraction varied using different flow rates and residence times for contact between fluorescein or fluorescein-BSA with the anti-fluorescein RAM column. It was found that 90% of the fluorescein was extracted when using a contact time of 1.2 s and 80% fluorescein was extracted in 0.9 s. Although this rate of extraction was quite fast, it was slower than what has been noted for the same type of antibodies on more traditional silica-based immunoaffinity supports that have not been treated with papain. This difference may be due to the decreased amount of $F_{ab}$ regions present in the anti-fluorescein RAM support versus these other materials. Under the same conditions used for fluorescein, less than 1% of the fluorescein-BSA conjugate was extracted by the anti-fluorescein RAM support. Thus, a RAM support may be quite selective for a low mass versus high mass target when used under these conditions.

Example 13

Method for Preparing Restricted Access Media with a Protected and Unbound Ligand Binding Agent or Enzyme Molecule A Nucleosil silica support was converted into a hydrazide-activated form by treating a 500 mg quantity of the support with 3-glycidoxypropyltrimethoxysilane to introduce epoxy groups onto the silica. The resulting epoxy silica support was treated with 0.1 M sodium acetate buffer (pH 5.5) by sonication under vacuum for 10-15 minutes. 3-Glycidoxypropyltrimethoxysilane (5%-10% v/v) was added to the suspension and shaken for 5 hours at 90° C. The epoxy silica support was washed several times with water and an aqueous solution of sulfuric acid (pH 3.0). The epoxy silica support was then suspended in 100-150 mL of an aqueous sulfuric acid solution (pH 3.0) and refluxed for one hour to convert the epoxy silica support into a diol form. The resulting diol silica support was washed with several portions of water, methanol and ether. The diol content of the diol silica support was determined using an iodometric capillary electrophoresis assay.

The diol silica support was used to prepare an aldehyde-activated silica support. To convert the diol groups to aldehyde groups, 500 mg of the diol silica support was suspended in 10 mL of a 90% (v/v) mixture of acetic acid and water that contained 500 mg periodic acid. This mixture was sonicated under vacuum for 20 minutes and shaken on a wrist-action shaker for 2 hours at room temperature. The resulting aldehyde-activated silica was washed several times with water and, 0.10 M potassium phosphate buffer (pH 6.0). A 200 mg quantity of the aldehyde-activated silica support was suspended in 30 mL of 0.10 M potassium phosphate buffer (pH 5.0) that contained a 5-fold mole excess of oxalic dihydrazide versus the initial diol groups present in the added aldehyde-activated silica support. The slurry was shaken for 2 hours at room temperature on a wrist-action shaker. The support was then washed several times with 0.10 M potassium phosphate buffer (pH 7.0). After activation, a 25-fold mol excess of sodium borohydride (versus the initial diol groups) in 4 mL of 0.10 M potassium phosphate buffer (pH 8.0) was added in several small portions to the support slurry to reduce any remaining aldehyde groups. This mixture was shaken for 90 minutes at room temperature and washed several times with 0.10 M potassium phosphate buffer (pH 7.0). The final hydrazide-activated support was stored in 0.10 M potassium phosphate buffer (pH 7.0) at 4° C. until use.

Glycogen was oxidized for use as the oxidized polysaccharide by reacting a 5 mg/mL glycogen solution with a 20 mg/mL solution of periodate for 12 hours at room temperature in a solution containing 20 mM sodium acetate, 0.15 mM sodium chloride (pH 7.0). The oxidized glycogen was purified using an Econo-Pac 10DG disposable column and 0.1 M potassium phosphate buffer (pH 5.0).

Example 14

Restricted Access Media with Protected and Unbound Human Serum Albumin

A 50 mg/mL human serum albumin ("HSA") solution was prepared in the 20 mM sodium acetate, 0.15 mM sodium chloride (pH 7.0) solution. A 0.03 g quantity of hydrazide-activated silica support was mixed with 0.5 mL of the 50 mg/mL HSA solution and sonicated under vacuum for 15 minutes. A 100 μL quantity of purified oxidized glycogen was added to the support-HSA mixture and shaken for 24 hours at room temperature. A 0.2 mL volume of a 2 mg/mL oxalic dihydrazide solution was added during the last hour of the reaction to cover any remaining aldehyde groups on the oxidized glycogen. The support was then washed several times with 0.1 M potassium phosphate solution (pH 7.0) and deionized water. Two control supports were prepared in the same manner but with no HSA or no oxidized glycogen added to the hydrazide-activated silica. After preparation, the HSA and control supports were placed into separate 50 mm×2.1 mm I.D. stainless steel columns using 0.067 M phosphate buffer (pH 7.4).

Figure 10:
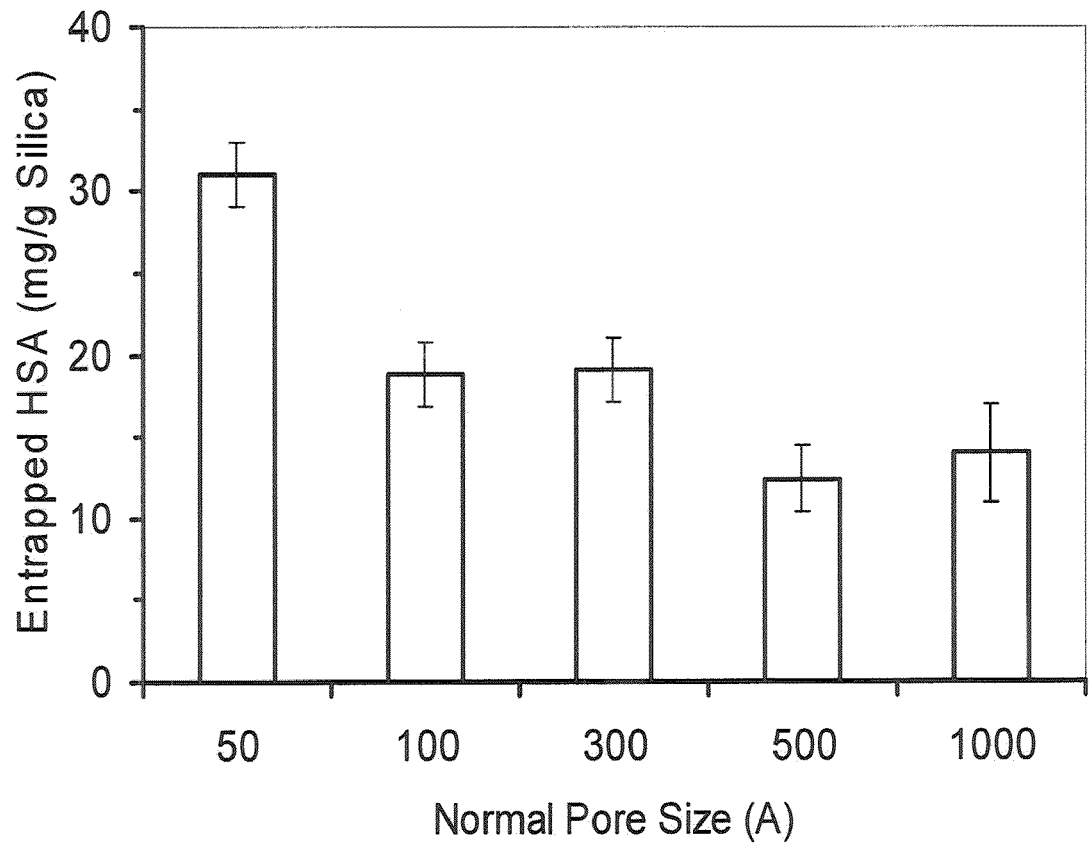
FIG. 10 is a graph showing the amount of human serum albumin (HSA) retained using a hydrazide-activated support with pore sizes ranging from 50 Å to 1000 Å.

As shown in FIG. 10, supports with pore sizes below 300 Å retained more HSA than larger pore size silica (500 Å and 1000 Å). Supports with 50 Å pore size had the greatest amount of retained HSA. Without being held to a particular theory, the size of the glycogen capping agent may prevent it from getting into pores smaller than 300 Å, making it easier for glycogen to cap such pores. As the pore size increased, glycogen may have entered a greater number of pores, giving a much smaller available volume for HSA retention.

Example 15

Restricted Access Media with Protected and Unbound Alpha 1-Acid Glycoprotein

A similar process used for obtaining restricted access media with protected and unbound HSA was used to obtain restricted access media with protected and unbound alpha 1-acid glycoprotein ("AGP"). A 25 mg sample of AGP was dissolved in 0.5 mL volume of a 4.2 mg/mL oxidized glycogen in 0.1 M potassium phosphate buffer (pH 5). The AGP/oxidized glycogen mixture was incubated with 0.15 g of hydrazide-activated silica support having 100 Å pore size for 2 days at 4° C. The support was washed several times with 0.1 M potassium phosphate buffer (pH 7) and packed into a 10×2.1 mm I.D. stainless steel column using 0.067 M phosphate buffer (pH 7.4) as the packing solution. Two control supports were prepared in the same manner but with no AGP or no oxidized glycogen added to the hydrazide-activated silica during the retention step.

Example 16

Activity of Protected and Unbound HSA in Restricted Access Media

Restricted access media with protected and unbound HSA was examined for HSA activity using S-warfarin, which is known to bind HSA. The binding capacities for the protected and unbound HSA columns are summarized in Table 1. Using the known content of HSA of these supports and the binding capacities, the specific activity for the retained HSA was determined. See, Table 1. The average specific activity was 91 (±29)%. This value was statistically equivalent to 100% and significantly higher than the specific activity reported for covalently immobilized HSA (see, Loun et al. 66 *Anal. Chem.* 3814-3822 (1994)). Association equilibrium constants also were determined for S-warfarin with retained HSA. Results are summarized in Table 1. Values ranged between 1.4 and $2.0 \times 10^5$ $M^{-1}$ at pH 7.4 at 37° C. These values were in good agreement with those reported for soluble HSA and immobilized HSA (e.g., $2.0 \times 10^5$ $M^{-1}$) (see, Loun et al. 66 *Anal. Chem.* 3814-3822 (1994)).

TABLE 1

Binding capacity and specific activity for S-warfarin on HSA Retained RAM columns.

| Pore Size | Binding Capacity ($\times 10^{-8}$ mol) | Specific Activity | Association Equilibrium Constant ($\times 10^5$ $M^{-1}$) |
|---|---|---|---|
| 1000 Å | 1.3 (+/−0.2) | 1.1 (+/−0.2) | 2.0 (+/−0.3) |
| 500 Å | 1.8 (+/−0.2) | 1.29 (+/−0.17) | 1.4 (+/−0.2) |
| 300 Å | 1.6 (+/−0.2) | 0.73 (+/−0.11) | 1.5 (+/−0.2) |
| 100 Å | 1.8 (+/−0.2) | 0.85 (+/−0.11) | N/A |
| 50 Å | 2.1 (+/−0.2) | 0.56 (+/−0.11) | 1.9 (+/−0.2) |

The discussion of the references herein is intended merely to summarize the assertions made by their authors and no admission is made that any reference constitutes prior art. Applicant reserves the right to challenge the accuracy and pertinence of the cited references.

In view of the above, it will be seen that the several advantages of the invention are achieved and other advantageous results attained. As various changes could be made in the above methods and compositions without departing from the scope of the invention, it is intended that all matter contained in the above description and shown in the accompanying drawings shall be interpreted as illustrative and not limiting. Thus, the breadth and scope of the present invention should not be limited by any of the above-described exemplary embodiments, but should be defined only in accordance with the following claims appended hereto and their equivalents.

What is claimed is:

1. A restricted access media comprising a support wherein a plurality of protected regions of said support contain one or more unbound ligand binding agent(s) or enzyme molecules, and wherein said unbound ligand binding agent(s) or enzyme molecule(s) are retained in said protected regions by a capping agent that is bound to said support, and wherein said ligand binding agent(s) or enzyme molecule(s) are not bound to said support.

2. The restricted access media of claim 1, wherein said support comprises an inorganic material, a biological material, an organic material, an organic polymer, a composite support, or a modified support.

3. The restricted access media of claim 1, wherein said unbound ligand binding agent comprises a protein, a glycoprotein, a DNA, a RNA, a nucleoprotein, a carbohydrate containing agent, a lipoprotein, or a combination thereof.

4. The restricted access media of claim 1, wherein said capping agent comprises a glycoprotein, a glycolipid, a carbohydrate containing agent, or a combination thereof.

5. The restricted access media of claim 4, wherein said carbohydrate containing agent comprises glycogen, dextran, agarose, or cellulose.

6. A method for preparing a restricted access media comprising:
   a) incubating an activated support with a solution comprising: i) a ligand binding agent or an enzyme molecule and
      ii) an activated capping agent; and
   b) removing unbound capping agent from said incubated support, thereby preparing the restricted access media comprising a support wherein a plurality of protected regions of said support contain one or more unbound ligand binding agent(s) or enzyme molecule(s)$_1$ and wherein said unbound ligand binding agent(s) or enzyme molecule(s) are retained in said protected regions by said capping agent that is bound to said support, and wherein said ligand binding agent(s) or enzyme molecule(s) are not bound to said support.

7. The method of claim 6, wherein said ligand binding agent or said enzyme molecule and said activated capping agent are incubated together or separately with said activated support.

8. The method of claim 6, wherein said activated support is activated by a hydrazide group, an amine group, an aldehyde group, or a combination thereof.

9. The method of claim 6, wherein said unbound ligand binding agent or enzyme molecule comprises a protein, a glycoprotein, a DNA, a RNA, a nucleoprotein, a carbohydrate containing agent, a lipoprotein, or a combination thereof.

10. The method of claim 6, wherein said support comprises a porous support with a pore size of about 50 Å to about 1000 Å.

11. A kit comprising a restricted access media that comprises comprising: i) a support wherein a plurality of protected regions of said support contain one or more unbound ligand binding agent or enzyme molecules, and wherein said ligand binding agent(s) or enzyme molecules are retained in said protected regions by a capping agent that is bound to said support, and wherein said ligand binding agent(s) or enzyme molecule(s) are not bound to said support, and ii) at least one container.

* * * * *